(12) United States Patent
Bhunia

(10) Patent No.: US 8,095,205 B2
(45) Date of Patent: *Jan. 10, 2012

(54) METHOD AND APPARATUS FOR VERIFYING A DETERMINED CARDIAC EVENT IN A MEDICAL DEVICE BASED ON DETECTED VARIATION IN HEMODYNAMIC STATUS

(75) Inventor: Sourav Bhunia, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1006 days.

This patent is subject to a terminal disclaimer.

(21) Appl. No.: 11/380,855

(22) Filed: Apr. 28, 2006

(65) Prior Publication Data

US 2007/0239053 A1    Oct. 11, 2007

Related U.S. Application Data

(60) Provisional application No. 60/787,765, filed on Mar. 31, 2006.

(51) Int. Cl.
*A61B 5/0432* (2006.01)

(52) U.S. Cl. .............. 600/509; 607/17; 607/18; 607/19; 607/20; 607/21; 607/22; 600/508

(58) Field of Classification Search .............. 607/17–22; 600/508–509

See application file for complete search history.

(56) References Cited

U.S. PATENT DOCUMENTS

| | | | |
|---|---|---|---|
| 4,180,078 A | 12/1979 | Anderson | |
| 4,202,339 A | 5/1980 | Wirtzfeld et al. | |
| 4,399,820 A | 8/1983 | Wirtzfeld et al. | |
| 4,467,807 A | 8/1984 | Bornzin | |
| 4,548,209 A | 10/1985 | Wielders et al. | |
| 4,567,892 A | 2/1986 | Plicchi et al. | |
| 4,750,495 A | 6/1988 | Moore et al. | |
| 5,163,427 A | 11/1992 | Keimel | |
| 5,176,137 A * | 1/1993 | Erickson et al. | 607/4 |
| 5,188,105 A | 2/1993 | Keimel | |
| 5,193,535 A | 3/1993 | Bardy et al. | |
| 5,364,316 A | 11/1994 | Brambilla | |
| 5,398,680 A * | 3/1995 | Polson et al. | 600/323 |
| 5,470,345 A | 11/1995 | Hassler et al. | |
| 5,545,186 A | 8/1996 | Olson et al. | |
| 5,596,986 A | 1/1997 | Goldfarb | |
| 5,683,432 A | 11/1997 | Goedeke et al. | |
| 5,855,593 A | 1/1999 | Olson et al. | |

(Continued)

OTHER PUBLICATIONS

International Search Report, PCTUS/2007/063895, Aug. 22, 2007, 6 Pages.

*Primary Examiner* — Niketa Patel
*Assistant Examiner* — Rex R Holmes
(74) *Attorney, Agent, or Firm* — Michael C. Soldner

(57) ABSTRACT

A method and apparatus for verifying a determined cardiac event in a medical device based on detected variation in hemodynamic status that includes a plurality of sensors sensing cardiac signals, and a physiologic sensor sensing physiologic signals to generate a plurality of variation index samples corresponding to the sensed signals. A microprocessor detects a cardiac event in response to the sensed cardiac signals, computes a variation index trend associated with a predetermined number of variation index samples of the plurality of variation index samples, determines whether the sensed cardiac signals are associated with noise in response to the computed variation index, and confirms the determined cardiac event in response to the sensed cardiac signals not being associated with noise.

14 Claims, 14 Drawing Sheets

U.S. PATENT DOCUMENTS

| | | |
|---|---|---|
| 6,144,866 A | 11/2000 | Miesel et al. |
| 6,198,952 B1 | 3/2001 | Miesel |
| 6,236,882 B1 * | 5/2001 | Lee et al. .................. 600/509 |
| 6,512,940 B1 | 1/2003 | Brabec et al. |
| 6,522,915 B1 | 2/2003 | Ceballos et al. |
| 6,622,046 B2 | 9/2003 | Fraley et al. |
| 6,944,488 B2 | 9/2005 | Roberts |
| 2005/0119586 A1 * | 6/2005 | Coyle et al. .................. 600/538 |

* cited by examiner

US 8,095,205 B2

METHOD AND APPARATUS FOR VERIFYING A DETERMINED CARDIAC EVENT IN A MEDICAL DEVICE BASED ON DETECTED VARIATION IN HEMODYNAMIC STATUS

RELATED APPLICATION

The present application claims priority and other benefits from U.S. Provisional Patent Application Ser. No. 60/787,765, filed Mar. 31, 2006, entitled "METHOD AND APPARATUS FOR VERIFYING A DETERMINED CARDIAC EVENT IN A MEDICAL DEVICE BASED ON DETECTED VARIATION IN HEMODYNAMIC STATUS", incorporated herein by reference in its entirety.

CROSS-REFERENCE TO RELATED APPLICATION

Cross-reference is hereby made to the commonly-assigned related U.S. Applications, U.S. patent application Ser. No. 11/380,859, entitled "METHOD AND APPARATUS FOR VERIFYING A DETERMINED CARDIAC EVENT IN A MEDICAL DEVICE BASED ON DETECTED VARIATION IN HEMODYNAMIC STATUS", to Bhunia; and U.S. patent application Ser. No. 11/380,849, entitled "METHOD AND APPARATUS FOR VERIFYING A DETERMINED CARDIAC EVENT IN A MEDICAL DEVICE BASED ON DETECTED VARIATION IN HEMODYNAMIC STATUS", to Bhunia, both filed concurrently herewith and incorporated herein by reference in their entirety.

FIELD OF THE INVENTION

The present invention relates generally to medical devices, and more particularly to a method and apparatus for confirming detection of a cardiac event based on the detection variations in hemodynamic status using an optical sensor.

BACKGROUND OF THE INVENTION

Implantable medical devices (IMDs) for monitoring a physiological condition or delivering a therapy typically rely on one or more sensors positioned in a patient's blood vessel, heart chamber, or other portion of the body. Examples of such medical devices include heart monitors, pacemakers, implantable cardioverter-defibrillators (ICDs), myostimulators, nerve stimulators, drug delivery devices, subcutaneous defibrillators, and other IMDs where such sensors are desirable. Implantable sensors used in conjunction with an IMD generally provide a signal related to a physiological condition from which a patient condition or the need for a therapy can be assessed.

Measurement of blood oxygen saturation levels are of interest in determining the metabolic state of the patient. Generally, a decrease in blood oxygen saturation is associated with an increase in physical activity or may reflect insufficient cardiac output or respiratory activity. Thus monitoring blood oxygen saturation allows an implantable medical device to respond to a decrease in oxygen saturation, for example by pacing the heart at a higher rate. An implantable oxygen sensor for use with an implantable medical device is generally disclosed in commonly assigned U.S. Pat. No. 6,198,952 issued to Miesel, hereby incorporated herein by reference in its entirety. Cardiac pacemakers that respond to changes in blood oxygen saturation as measured by an optical sensor are generally disclosed in U.S. Pat. No. 4,202,339 issued to Wirtzfeld and in U.S. Pat. No. 4,467,807 issued to Bornzin.

Practical applications for optical hemodynamic sensors, however, have been limited because such sensors are highly susceptible to motion; that is, movement by the patient or of the sensor tends to introduce significant noise onto an output signal of the sensor.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION OF THE INVENTION

Figure 1:
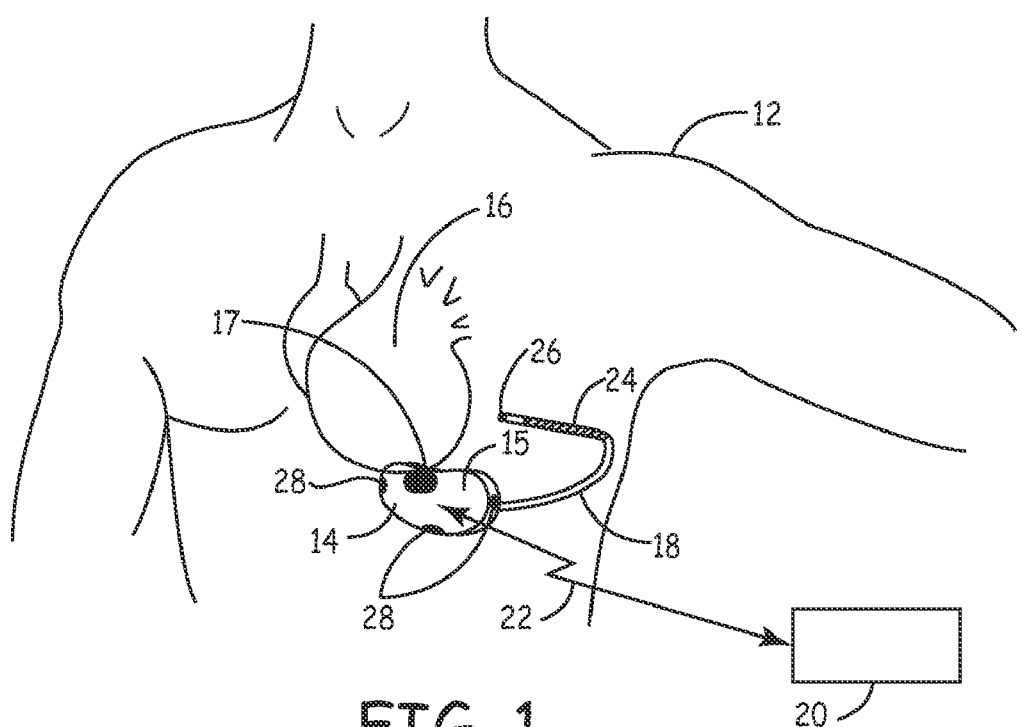
FIG. 1 is a schematic diagram of an exemplary medical device in which the present invention may be usefully practiced.

FIG. 1 is a schematic diagram of an exemplary medical device in which the present invention may be usefully practiced. As illustrated in FIG. 1, the present invention may be utilized in an implantable medical device 14 that includes a housing 15 containing circuitry for operating device 14 that is subcutaneously implanted in a patient, outside the ribcage of patient 12, anterior to the cardiac notch, for example. According to an embodiment of the present invention, housing 15 may be implanted in the pectoral region of the patient 12. Further, device 14 may include a subcutaneous sensing and cardioversion/defibrillation therapy delivery lead 18 coupled to the device 14 that is tunneled subcutaneously into a location adjacent to a portion of a latissimus dorsi muscle of patient 12. Specifically, lead 18 is tunneled subcutaneously from the median implant pocket of device 14 laterally and posterially to the patient's back to a location opposite the heart such that the heart 16 is disposed between the device 14 and the distal electrode coil 24 and distal sensing electrode 26 of lead 18.

It is understood that while the subcutaneous device 14 is shown positioned through loose connective tissue between the skin and muscle layer of the patient, the term "subcutaneous device" is intended to include a device that can be positioned in the patient to be implanted using any non-intravenous location of the patient, such as below the muscle layer or within the thoracic cavity, for example.

Further referring to FIG. 1, programmer 20 is shown in telemetric communication with SubQ ICD 14 by RF communication link 22. Communication link 22 may be any appropriate RF link such as Bluetooth, WiFi, MICS, or as described in U.S. Pat. No. 5,683,432 "Adaptive Performance-Optimizing Communication System for Communicating with an Implantable Medical Device" to Goedeke, et al and incorporated herein by reference in its entirety.

Device 14 may be constructed of stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multilayered Ceramic Enclosure" to Hassler, et al, both incorporated herein by reference in their entireties. The electronics circuitry of device 14 may be incorporated on a polyamide flex circuit, printed circuit board (PCB) or ceramic substrate with integrated circuits packaged in leadless chip carriers and/or chip scale packaging (CSP).

Lead 18, which is inserted within a connector (not shown) positioned on housing 15 to electrically coupled lead to the circuitry located in housing 15, includes a distal defibrillation coil electrode 24, a distal sensing electrode 26, an insulated flexible lead body and a proximal connector pin (not shown) for connection to housing 15 via the connector. Distal sensing electrode 26 is sized appropriately to match the sensing impedance of one or more electrodes 28 that are positioned along housing 15 to form a housing-based subcutaneous electrode array with electrodes 28 positioned to form orthogonal signal vectors.

Device 14 in is an exemplary graphical representation of an $O_2$ variation index trend utilized in a method of delivering a therapy in a medical device according to an embodiment of the present invention includes an optical sensor 17 positioned along the outer surface of housing 15, which is utilized to generate an $O_2$ variation index trend for use in generating a secondary confirmation of the detection of a cardiac event by the primary detection algorithm, as described in detail below. Electrodes 28 and optical sensor 17 are welded into place on the outer surface of the housing 15 and are connected via wires (not shown) to electronic circuitry (described herein below) located inside housing 15. Electrodes 28 may be constructed of flat plates, or alternatively, spiral electrodes as described in U.S. Pat. No. 6,512,940 "Subcutaneous Spiral Electrode for Sensing Electrical Signals of the Heart" to Brabec, et al and mounted in a non-conductive surround shroud as described in U.S. Pat. No. 6,522,915 "Surround Shroud Connector and Electrode Housings for a Subcutaneous Electrode Array and Leadless ECGs" to Ceballos, et al and U.S. Pat. No. 6,622,046 "Subcutaneous Sensing Feedthrough/Electrode Assembly" to Fraley, et al, all incorporated herein by reference in their entireties.

The electronic circuitry employed in device 14 can take any of the known forms that detect a tachyarrhythmia from the sensed ECG and provide cardioversion/defibrillation shocks as well as post-shock pacing as needed while the heart recovers. An exemplary simplified block diagram of such circuitry adapted to function employing the first and second cardioversion-defibrillation electrodes as well as the ECG sensing and pacing electrodes described herein below is set forth in FIG. 3. It will be understood that the simplified block diagram does not show all of the conventional components and circuitry of such devices including digital clocks and clock lines, low voltage power supply and supply lines for powering the circuits and providing pacing pulses or telemetry circuits for telemetry transmissions between the device 14 and external programmer 20.

Optical hemodynamic sensor 17 is preferably a multiple waveform oximeter, such as a pulse oximeter or a mixed-venous oxygen sensor, for example. Pulse oximeters are well known sensors commonly used with various medical devices, both implantable and external. For example, some applications of optical oximeters are disclosed in U.S. Pat. Nos. 4,750,495; 5,176,137; 6,144,866; 6,198,952; or 6,944,488, each of which is assigned to Medtronic, Inc.

Generally, optical oximeters include a light source for emitting light through a blood perfused tissue of patient P and a light detector for generating a signal representative of an intensity of light transmitted through the blood perfused tissue to the light detector. In other embodiments, the mixed-venous oxygen sensor may be placed in the blood stream itself. The light passed through the tissue or bloodstream is commonly selected to be of two or more wavelengths, and most commonly, the light is selected to fall in the red part of the visible light spectrum and the infrared (IR) portion of the light spectrum. The light transmitted through the blood perfused tissue or bloodstream and received by the light detector is generally representative of hemodynamic function.

Figure 2:
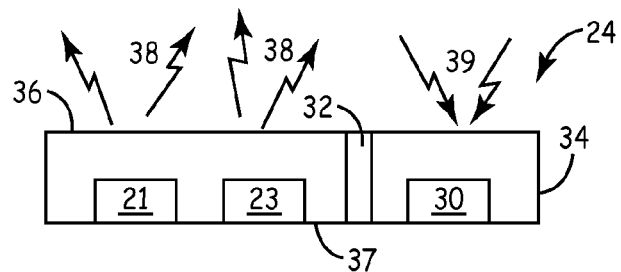
FIG. 2 is a schematic diagram of an optical hemodynamic sensor according to an embodiment of the present invention.

FIG. 2 is a schematic diagram of an optical hemodynamic sensor according to an embodiment of the present invention. As illustrated in FIG. 2 optical sensor 17 includes a red light emitting diode (LED) 21, an infrared (IR) LED 23, a photodiode 30, and an optical barrier 32, all of which are positioned within a sensor housing 34 having a lens 36. In the embodiment shown in FIG. 2, LEDs 21 and 23 and photodiode 30 are each mounted on a substrate 37, or a bottom surface of housing 34. As indicated by arrows 38, red and IR LEDs 21 and 23 are configured to emit light through lens 36 of housing 34, while, as indicated by arrows 39, photodiode 30 is configured to detect light received through lens 36. Optical barrier 32 is positioned to block direct transmission of light from LEDs 21 and 23 to photodiode 30.

Optical hemodynamic sensor 17 preferably is subcutaneously or submuscularly implanted within patient P such that lens 36 is oriented toward a blood perfused tissue of patient P.

Red LED 21 preferably emits light in the red portion of the visible light spectrum, while IR LED 23 preferably emits IR light in the IR portion of the light spectrum. In alternate embodiments, optical hemodynamic sensor 17 may include any two or more light sources for producing at least two different wavelengths of light. Photodiode 30 preferably receives light transmitted by LEDs 21 and 23, with an intensity of the signal received by photodiode 30 being indicative of hemodynamic function. For instance, oxygen saturation of the blood can be derived from an output of photodiode 30, as will be described below, and used to provide a secondary confirmation of a detected event by the device 14 according to the present invention.

Figure 3:
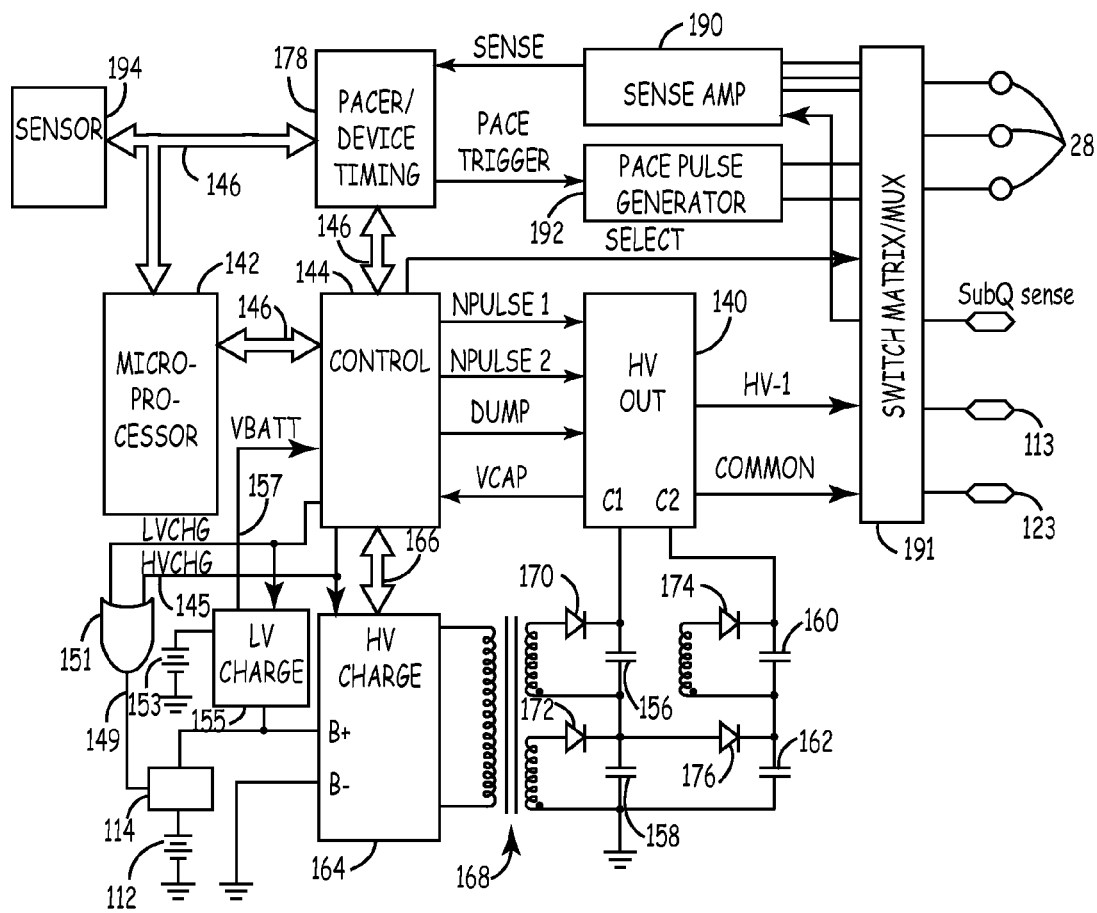
FIG. 3 is a schematic diagram of electronic circuitry included in the device of FIG. 1 according to an embodiment of the present invention.

FIG. 3 is a schematic diagram of electronic circuitry included in the device of FIG. 1 according to an embodiment of the present invention. As illustrated in FIG. 3, device 14 includes both a low voltage battery 153 and a high voltage battery 112, for example, positioned within the hermetically sealed housing 15 of the device 14. Low voltage battery 153 is coupled to a power supply (not shown) that supplies power to the device circuitry and the pacing output capacitors to supply pacing energy in a manner well known in the art. The low voltage battery 153 can include one or more conventional $LiCF_x$, $LiMnO_2$ or $LiI_2$ cells, while the high voltage battery 112 can include one or more conventional LiSVO or $LiMnO_2$ cells. It is understood that although the exemplary embodiment of FIG. 3 includes both low and high power therapy, the present invention may be employed in a device that provides only one therapy, such as a high power defibrillation therapy, for example.

Device 14 functions are controlled by means of software, firmware and hardware that cooperatively monitor the ECG, determine when a cardioversion-defibrillation shock or pacing is necessary, and deliver prescribed cardioversion-defibrillation and pacing therapies. FIG. 3 incorporates circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel for selectively delivering single phase, simultaneous biphasic and sequential biphasic cardioversion-defibrillation shocks, incorporated herein by reference in their entireties In FIG. 3, sense amp 190 in conjunction with pacer/device timing circuit 178 processes the far field ECG sense signal that is developed across a particular ECG sense vector defined by a selected pair of the subcutaneous electrodes 28 or, optionally, a virtual signal if selected. The selection of the sensing electrode pair is made through the switch matrix/MUX 191 in a manner to provide the most reliable sensing of the EGM signal of interest, which would be the R wave for patients who are believed to be at risk of ventricular fibrillation leading to sudden death. The far field ECG signals are passed through the switch matrix/MUX 191 to the input of the sense amplifier 190 that, in conjunction with pacer/device timing circuit 178, evaluates the sensed EGM. Bradycardia, or a systole, is typically determined by an escape interval timer within the pacer timing circuit 178 and/or the control circuit 144. Pace Trigger signals are applied to the pacing pulse generator 192 generating pacing stimulation when the interval between successive R-waves exceeds the escape interval. Bradycardia pacing is often temporarily provided to maintain cardiac output after delivery of a cardioversion-defibrillation shock that may cause the heart to slowly beat as it recovers back to normal function. Sensing subcutaneous far field signals in the presence of noise may be aided by the use of appropriate denial and extensible accommodation periods as described in U.S. Pat. No. 6,236,882 "Noise Rejection for Monitoring ECGs" to Lee, et al and incorporated herein by reference in its' entirety.

Detection of a malignant tachyarrhythmia is determined in the control circuit 144, for example, as a function of the intervals between R-wave sense event signals that are output from the pacer/device timing 178 and sense amplifier circuit 190 to the timing and control circuit 144.

Supplemental sensors such as tissue color, tissue oxygenation, respiration, patient activity and the like may be used to contribute to the decision to apply or withhold a defibrillation therapy as described generally in U.S. Pat. No. 5,464,434 "Medical Interventional Device Responsive to Sudden Hemodynamic Change" to Alt and incorporated herein by reference in its entirety. In particular, the present invention includes optical sensor 17 to provide a secondary confirmation of a detected tachyarrhythmia event detected by the device 14 by determining whether the heart is hemodynamically unstable in response to a tachycardia event being identified by the device 15 in response to R-wave sense intervals determined in the primary detection algorithm, described below in detail. Sensor processing unit 194 provides sensor data to microprocessor 142 via data bus 146. In addition to optical sensor 17, an activity sensor may also be utilized so that patient activity and/or posture may also be determined by the apparatus and method as described in U.S. Pat. No. 5,593,431 "Medical Service Employing Multiple DC Accelerometers for Patient Activity and Posture Sensing and Method" to Sheldon and incorporated herein by reference in its entirety. Similarly, patient respiration may be determined by the apparatus and method as described in U.S. Pat. No. 4,567,892 "Implantable Cardiac Pacemaker" to Plicchi, et al and incorporated herein by reference in its entirety. As mentioned above, according to the present invention, optical sensor 17 may be located on the housing 15 of device 14, or may be located on the lead 18 to enable the sensing of contacting or near-contacting tissue oxygenation.

Certain steps in the performance of the detection algorithm criteria are cooperatively performed in microcomputer 142, including microprocessor, RAM and ROM, associated circuitry, and stored detection criteria that may be programmed into RAM via a telemetry interface (not shown) conventional in the art. Data and commands are exchanged between microcomputer 142 and timing and control circuit 144, pacer timing/amplifier circuit 178, and high voltage output circuit 140 via a bi-directional data/control bus 146. The pacer timing/amplifier circuit 178 and the control circuit 144 are clocked at a slow clock rate. The microcomputer 142 is normally asleep, but is awakened and operated by a fast clock by interrupts developed by each R-wave sense event, on receipt of a down-link telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

The algorithms and functions of the microcomputer 142 and control circuit 144 employed and performed in detection of tachyarrhythmias are set forth, for example, in commonly assigned U.S. Pat. No. 5,354,316 "Method and Apparatus for Detection and Treatment of Tachycardia and Fibrillation" to Keimel; U.S. Pat. No. 5,545,186 "Prioritized Rule Based Method and Apparatus for Diagnosis and Treatment of Arrhythmias" to Olson, et al, U.S. Pat. No. 5,855,593 "Prioritized Rule Based Method and Apparatus for Diagnosis and Treatment of Arrhythmias" to Olson, et al and U.S. Pat. No. 5,193,535 "Method and Apparatus for Discrimination of Ventricular Tachycardia from Ventricular Fibrillation and Treatment Thereof" to Bardy, et al, (all incorporated herein by reference in their entireties). Particular algorithms for detection of ventricular fibrillation and malignant ventricular tachycardias can be selected from among the comprehensive algorithms for distinguishing atrial and ventricular tachyarrhythmias from one another and from high rate sinus rhythms that are set forth in the '316, '186, '593 and '593 patents.

The detection algorithms are highly sensitive and specific for the presence or absence of life threatening ventricular arrhythmias, e.g., ventricular tachycardia (VT) and ventricular fibrillation (VF). When a malignant tachycardia is detected, high voltage capacitors 156, 158, 160, and 162 are charged to a preprogrammed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bi-directional control/data bus 166 and a feedback signal VCAP from the HV output circuit 140. High voltage output capacitors 156, 158, 160 and 162 may be of film, aluminum electrolytic or wet tantalum construction.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 149 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 700-3150V, to be discharged through the body and heart between the electrode pair of subcutaneous cardioversion-defibrillation electrodes 113 and 123. The details of the voltage charging circuitry are also not deemed to be critical with regard to practicing the present invention; one high voltage charging circuit believed to be suitable for the purposes of the present invention is disclosed. High voltage capacitors 156, 158, 160 and 162 are charged by high voltage charge circuit 164 and a high frequency, high-voltage transformer 168 as described in detail in commonly assigned U.S. Pat. No. 4,548,209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates the high voltage charge command HVCHG when the VCAP signal matches the programmed capacitor output voltage, i.e., the cardioversion-defibrillation peak shock voltage.

Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy cardioversion-defibrillation shocks between the pair of the cardioversion-defibrillation electrodes 113 and 123 coupled to the HV-1 and COMMON output as shown in FIG. 3.

Thus, device 14 monitors the patient's cardiac status and initiates the delivery of a cardioversion-defibrillation shock through the cardioversion-defibrillation electrodes 113 and 123 in response to detection of a tachyarrhythmia requiring cardioversion-defibrillation. The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. Typically, the charging cycle takes only fifteen to twenty seconds, and occurs very infrequently. The device 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock may be stored in RAM for uplink telemetry transmission to an external programmer as is well known in the art to facilitate in diagnosis of the patient's cardiac state. A patient receiving the device 14 on a prophylactic basis would be instructed to report each such episode to the attending physician for further evaluation of the patient's condition and assessment for the need for implantation of a more sophisticated implantable cardio-defibrillator device (ICD). In other embodiments, no storage of episode data will take place.

Figure 4:
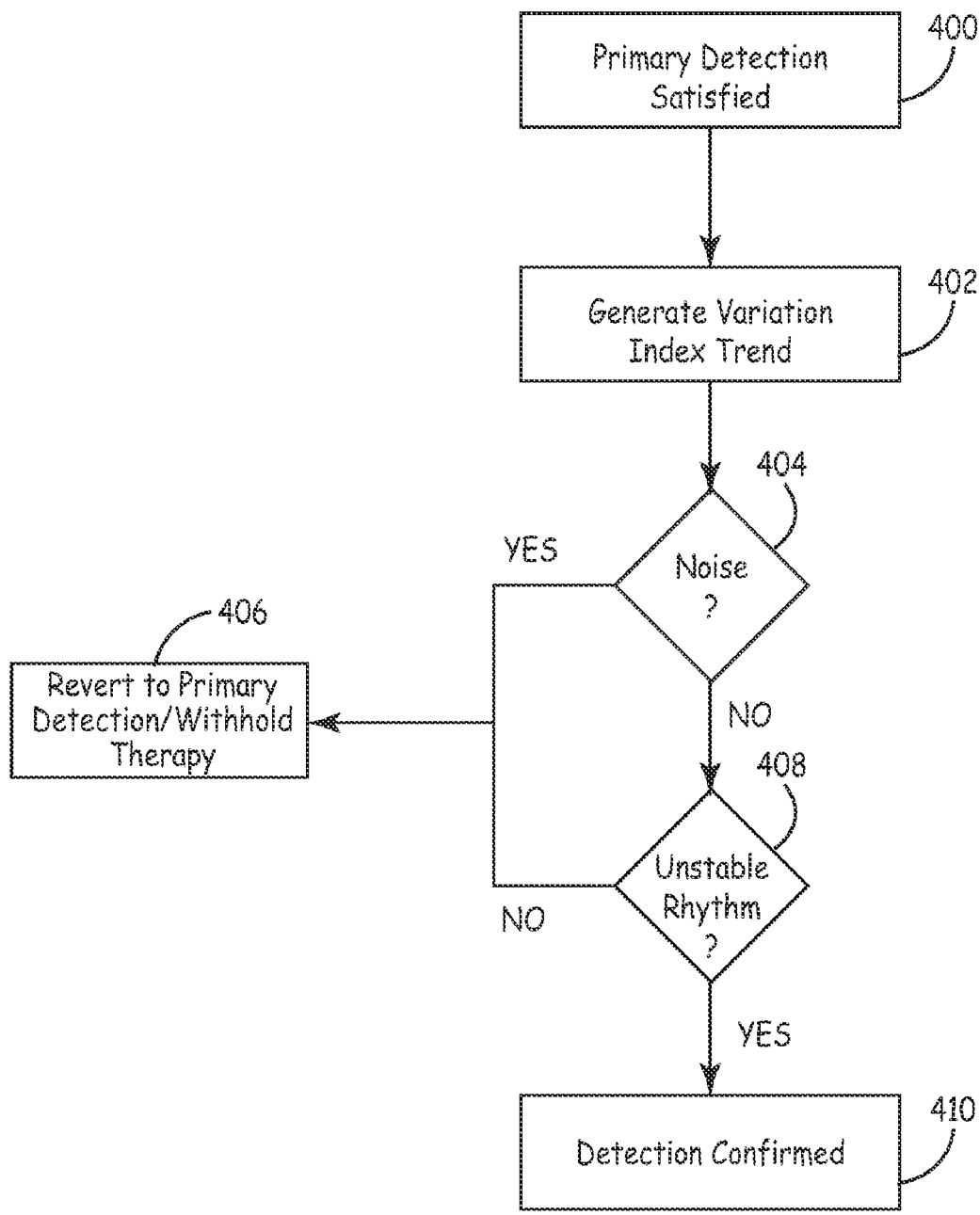
FIG. 4 is a flow chart of a method of delivering a therapy in a medical device according to an embodiment of the present invention.

FIG. 4 is a flow chart of a method of delivering a therapy in a medical device according to an embodiment of the present invention. As illustrated in FIG. 4, once control circuit 144 determines the presence of a malignant cardiac event using the primary detection algorithm described above, Block 400, the present invention generates a secondary confirmation of the event detected by the primary detection algorithm, blocks 402-410. In particular, once the primary detection algorithm is satisfied, the present invention utilizes the input generated from optical sensor 17 at multiple wavelengths to identify an $O_2$ variation index trend, block 402, as described below in detail. According to the present invention, the $O_2$ variation index trend is a measure of the change in tissue oxygenation and corresponds to the relationship between changes in both the volume of blood at the sensor site and the concentration of oxygenated hemoglobin (Hb $O_2$).

Using the results of the generated $O_2$ variation index trend, a determination is made as to whether the detected event is associated with noise, resulting from patient motion, for example, Block 404. If it is determined that the detected event is associated with noise, delivery of therapy is withheld, or control of the device is reverted back to the primary detection algorithm, Block 406. However, if it is determined that the detected event is not associated with noise, a determination is made as to whether the detected event is associated with an unstable rhythm, Block 408, such as ventricular tachycardia or ventricular fibrillation, for example.

If the detected event is not determined to be associated with an unstable rhythm, the result of the primary detection scheme is not confirmed and delivery of therapy is withheld or control of the device is reverted back to the primary detection algorithm, Block 406. If the detected event is determined to be associated with an unstable rhythm, the primary detection of the malignant event is confirmed, Block 410, and therapy is delivered.

Figure 5:
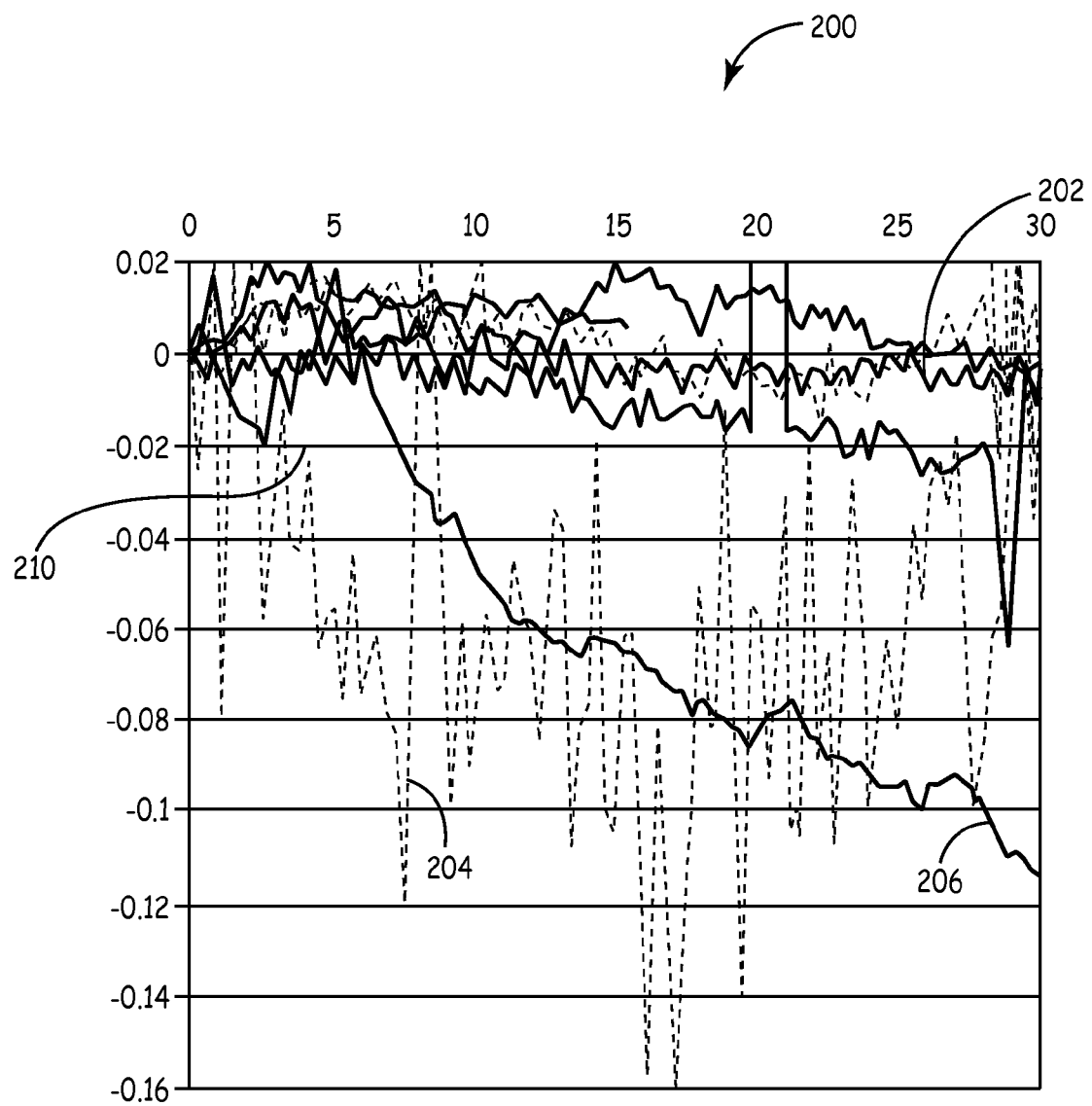
FIG. 5 is a graphical representation of identification of an exemplary $O_2$ variation index trend utilized in a method of delivering a therapy in a medical device according to an embodiment of the present invention.

FIG. 5 is a graphical representation of identification of an exemplary $O_2$ variation index trend utilized in a method of delivering a therapy in a medical device according to an embodiment of the present invention. As illustrated in FIG. 5, once control circuit 144 determines the presence of a cardiac event, such as ventricular tachycardia or ventricular fibrillation, for example, using the primary detection algorithm described above, the presence of the cardiac event is confirmed by determining changes in blood oxygenation of the patient. The changes in blood oxygenation are determined using an $O_2$ variation index trend 200 that is identified based on the intensity readings associated with the intensity of the red light emitted by red LED 21 and the infrared light emitted by infrared LED 23 that is received at photodiode 30.

In particular, in order to identify the $O_2$ variation index trend 200, both a red light baseline intensity $i_0$ and an infrared light baseline intensity $i^*_0$ is identified from sample outputs received at a predetermined sample rate over a sampling time interval. For example, according to an embodiment of the present invention, sample outputs are received at photodiode 30 from red LED 21 and infrared LED 23 at a sampling rate of three samples per second over a two second sampling time interval. Baseline intensity $i_0$ and baseline intensity $i^*_0$ are then determined from the sample outputs from red LED 21 and infrared LED 23, respectively. For example, according to an embodiment of the present invention, baseline intensity $i_0$ and baseline intensity $i^*_0$ are determined, respectively, by setting baseline intensity $i_0$ equal to the average of the sample outputs from red LED 21 over a predetermined time period and setting baseline intensity $i^*_0$ equal to the average of the sample outputs from infrared LED 23 over the predetermined time period.

Once the red and infrared baseline intensities $i_0$ and $i^*_0$ have been determined, a variation index is determined for each subsequently received two-wavelength sample output by sensor 17 using an oxygen variation index equation:

$$\text{Variation index} = \frac{i}{i_0} - \frac{i^*}{i^*_0} \quad \text{Equation 1}$$

where i is the intensity of red light from red LED 21 incident on photodetector 30 for a given sample and i* is the intensity of infrared light from infrared LED 21 incident on photodetector 30 for the same sample. In this way, the variation index for each two-wavelength sample output is the difference between the proportion of the red and the infrared intensity signals with respect to their corresponding baseline intensities. Using the exemplary sampling rate of 3 Hz, three variation indexes are generated each second and are used to determine the $O_2$ variation index trend 200.

It is understood that other relationships between the proportions of the red and infrared intensities to their corresponding baseline intensities $i/i_0$ and $i^*/i^*_0$. For example, if the proportion of the red intensity signal to the baseline red intensity $\frac{i}{i_0}$ is referred to as the normalized red intensity and the proportion of the infrared intensity signal to the baseline infrared intensity $i^*/i^*_0$ is referred to as the normalized infrared intensity, Equation 1 may alternatively be a ratio of the normalized red and infrared intensities, or may be a difference between the unequally weighted red and infrared normalized intensities.

FIG. 5 includes three oxygen variation index trends identified using the oxygen variation index equation, Equation 1. The first is an exemplary $O_2$ variation index trend resulting during normal sinus rhythm 202, the second is an exemplary $O_2$ variation index trend resulting during noise 204, such as patient motion for example, and the third is an exemplary $O_2$ variation index trend resulting during a malignant cardiac event 206, such as ventricular fibrillation for example. As can be seen in FIG. 5, using the $O_2$ variation index trend 200 identified according to the present invention, the $O_2$ variation index trend resulting during noise 204 tends to exhibit a variability that is significantly greater than the variability exhibited by the $O_2$ variation index trend resulting during normal sinus rhythm 202, while the $O_2$ variation index trend resulting during the malignant cardiac event 206 tends to exhibit a variability that is generally equivalent to or less than the variability exhibited by the $O_2$ variation index trend resulting during normal sinus rhythm 202. As described below, the present invention utilizes these variation features and others to perform a secondary confirmation of a cardiac event determined by a primary detection scheme to be a malignant cardiac event. One such criterion involves crossing of a predetermined baseline 210 by a parameter, described in detail below.

Figure 6:
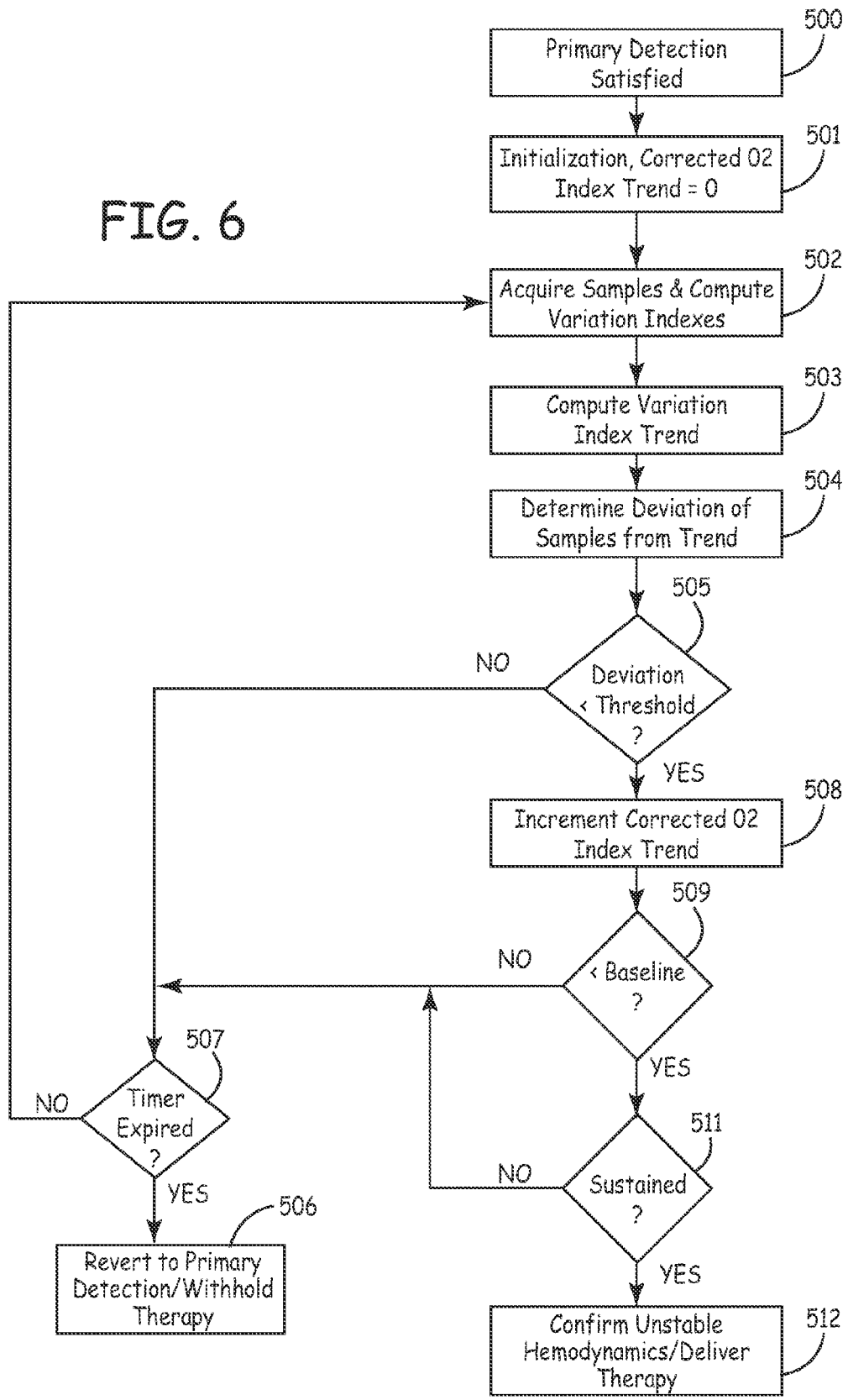
FIG. 6 is a flow chart of a method of delivering a therapy in a medical device according to an embodiment of the present invention.
Figure 7:
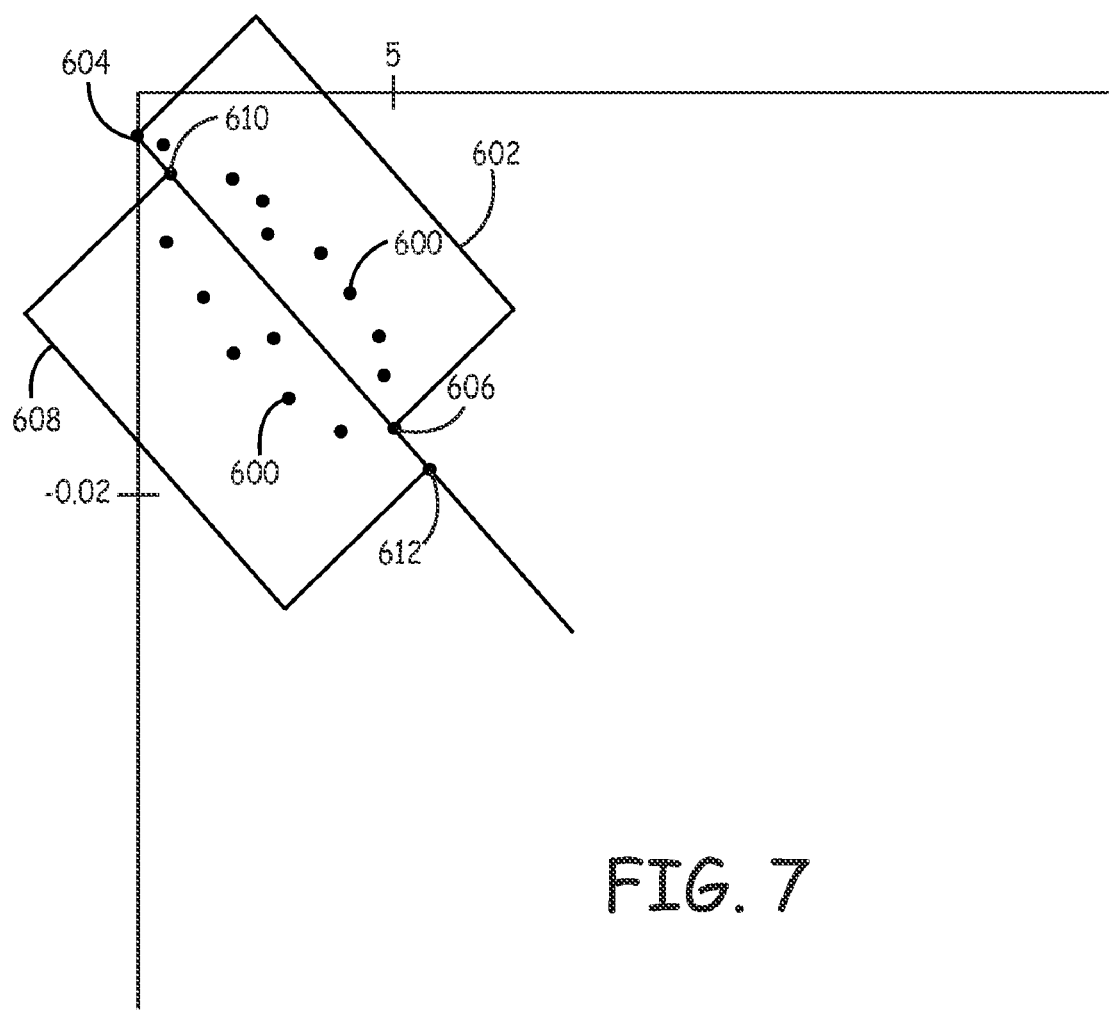
FIG. 7 is an exemplary $O_2$ variation index trend identified in a method of delivering a therapy in a medical device according to an embodiment of the present invention.

FIG. 6 is a flow chart of a method of delivering a therapy in a medical device according to an embodiment of the present invention. FIG. 7 is an exemplary $O_2$ variation index trend identified in a method of delivering a therapy in a medical device according to an embodiment of the present invention. As illustrated in FIGS. 6 and 7, once the primary detection algorithm is satisfied, Yes in Block 500, the present invention begins with the initialization of several parameters, such as a corrected $O_2$ index trend, Block 501, which is intended to represent a measure of the change in tissue oxygenation and will be utilized below in reference to Block 508.

Once the initialization of parameters is complete, i.e., the corrected $O_2$ index trend is set equal to zero, the present invention begins computing $O_2$ variation indexes 600 using the optical sample inputs from optical sensor 17 at multiple wavelengths and Equation 1, Block 502. Optical sample inputs from sensor 17 are collected and the corresponding $O_2$ variation indexes 600 are computed using Equation 1 for a predetermined sample collection period. The predetermined sample collection period may be set as a predetermined period of time, such as 5 seconds, for example, or may be set as a predetermined number of samples, such as 15, for example. In the an exemplary trend according to the present invention, the sample rate of 3 Hz is utilized and the sample collection period is set as five seconds, for example, so that 15 $O_2$ variation indexes 600 are determined over each sample collection period.

At the end of the initial sample collection period, an $O_2$ variation index trend 602 is identified for the sample collection period, Block 503, and a measure of the deviation of each of the acquired $O_2$ variation indexes 600 occurring during the current sample collection period from the $O_2$ variation index trend 602 is determined, Block 504. According to an embodiment of the present invention, the $O_2$ variation index trend 602 is identified in Block 503 by performing a least square linear fit of the acquired $O_2$ variation indexes 600 during the sample collection period, i.e., the first through the $15^{th}$ $O_2$ variation indexes $O_{2(1)}$-$O_{2(15)}$, so that the resulting trend has a start point 604 where the first $O_2$ variation index $O_{2(1)}$ is projected onto the $O_2$ variation index trend 602 and an endpoint 606 where the last $O_2$ variation index $O_{2(15)}$ is projected onto the $O_2$ variation index trend 602, i.e., the $15^{th}$ $O_2$ variation index 600, and the measure of deviation of the current samples from the trend, Block 504, is performed by determining the mean square deviation of the $O_2$ variation indexes 600 in the current window of $O_2$ variation indexes from the $O_2$ variation index trend 602.

According to an embodiment of the present invention, the $O_2$ variation index trend 602 may be obtained, for example, by an alternative filtering technique and the measure of the deviation of the indexes 600 from the $O_2$ variation index trend 602 may be determined as the mean square of the indexes 600 from the filtered index trend.

In order to perform the secondary determination of whether the detected event is associated with noise (Block 404 of FIG. 4), once the deviation of the associated $O_2$ variation indexes 600 from the current $O_2$ variation index trend is determined, Block 504, a determination is then made as to whether the deviation is less than a predetermined deviation threshold, Block 505.

If the deviation of the $O_2$ variation indexes 600 for the current window of $O_2$ variation indexes 600 is not less than or is equal to the deviation threshold, No in Block 505, indicating a likelihood that the determined cardiac event may be the result of noise, a determination is made as to whether a predetermined episode verification time period has expired, Block 507. If the episode verification time period has not expired, the process returns to Block 502 so that the deviation of $O_2$ variation indexes from the $O_2$ variation index trend, Blocks 503 and 504, is determined for the next window of $O_2$ variation indexes 600.

In particular, once the deviation of the $O_2$ variation indexes 600 for the current window of $O_2$ variation indexes is determined to be greater than the deviation threshold and the episode verification time period, No in Block 507, i.e., 30 seconds for example, has not expired, an $O_2$ variation index trend 608 is determined for the next window of $O_2$ variation indexes, i.e., the window including the $2^{nd}$ through the $16^{th}$ $O_2$ variation indexes $O_{2(2)}$-$O_{2(16)}$, so that the resulting trend has a start point 610 where the second $O_2$ variation index $O_{2(2)}$ is projected onto the $O_2$ variation index trend 608 and an endpoint 612 where the last $O_2$ variation index $O_{2(16)}$ is projected onto the $O_2$ variation index trend 608. The deviation of the $O_2$ variation indexes 600 for that window of $O_2$ variation indexes $O_{2(2)}$-$O_{2(16)}$ from the $O_2$ variation index trend 608 is determined and compared to the deviation threshold, Block 505. In this way, the process of the present invention continues to compute the $O_2$ variation index trend over a moving group of consecutive computed $O_2$ variation indexes including some of the most recently acquired samples, with the size of the group of samples being consistent with the sample collection period.

The process continues for the next window of $O_2$ variation indexes 600, and if the deviation of generated $O_2$ variation indexes 600 from the associated trends for the subsequent sample collections periods continues to be greater than the deviation threshold and therefore the episode verification time period has expired, the secondary confirmation process determines that the cardiac event is most likely related to noise, and therapy is withheld or control of the device is reverted back to the primary detection algorithm, Block 506.

The episode verification time period may be set at any desired value, so that the determination of whether the cardiac event is noise related may be made for a predetermined number of iterations or over a predetermined time period, depending on the chosen values for the sample collection period and the episode verification time period. For example, according to an embodiment of the present invention, the episode verification time period is set at 30 seconds and the sample collection period is set at 5 seconds. In this example, if the optical sensor signals are sampled a 3 Hz, ninety $O_2$ variation indexes are computed over the episode verification time period, with the associated $O_2$ variation index trend and deviation being computed every 5 seconds over a moving group of 15 consecutive samples. Since the computation of the $O_2$ variation index trend begins once 15 variation indexes are computed, the determination of whether a detected cardiac event is noise related, and if not, whether it is hemodynamically stable, Blocks 509 and 511, is made for seventy-six iterations, over each 30 second episode verification time period.

If the deviation of the $O_2$ variation indexes for a given window of $O_2$ variation indexes is determined to be less than the deviation threshold, Yes in Block 505, indicating a likelihood that the determined cardiac event is not the result of noise, the corrected $O_2$ index trend is incremented by the determined deviation of the current $O_2$ variation indexes, Block 508, as will be described in detail below. A determination is then made as to whether the current generated $O_2$ variation index trend 602 is less than a predetermined baseline value 210, Block 509.

According to the present invention, the baseline value 210 associated with Block 509 corresponds to a desired deviation associated with the relationship between the proportion of the intensity of red light i from LED 21 to the baseline intensity $i_0$ for LED 21, or $$\frac{i}{i_0}$$

of Equation 1, and the proportion of the intensity of infrared light i* from LED 23 to the baseline intensity $i^*_0$ for LED 23, or $$\frac{i^*}{i^*_0}$$

of Equation 1. For example, according to an embodiment of the present invention, the baseline value 210 is set as −0.02, corresponding to the proportion of the intensity of infrared light i* from LED 23 to the baseline intensity $i^*_0$ for LED 23 being greater than the proportion of the intensity of red light i from LED 21 to the baseline intensity $i_0$ for LED 21.

If the current $O_2$ variation index trend is not determined to be less than the predetermined baseline value 210, No in Block 509, indicating that while the determined cardiac event is not likely the result of noise, there is a likelihood that the determined cardiac event may be not be associated with an unstable rhythm, the determination is made as to whether the episode verification time period has expired, Block 507. If the episode verification time period has not expired, the process returns to Block 502 so that the deviation of $O_2$ variation indexes 600 is determined for the next window of $O_2$ variation indexes, block 503.

If the current $O_2$ variation index trend is determined to be less than the predetermined baseline value 210, indicating that the determined cardiac event is not likely the result of noise, and there is a likelihood that the determined cardiac event may be associated with an unstable rhythm, a determination is made as to whether the generated $O_2$ variation index trend is sustained, i.e., remains less than the predetermined baseline value 210 for a predetermined time period, such as 3 seconds for example, Block 511.

If the generated $O_2$ variation index trend is not sustained, i.e., not less than the predetermined baseline value 210 for the predetermined time period, the determination is made as to whether the episode verification time period has expired, Block 507. If the generated $O_2$ variation index trend is not sustained and the episode verification time period has not expired, the deviation of the generated $O_2$ variation indexes over the next window of $O_2$ variation indexes is determined, Blocks 503 and 504, and the noise determination is repeated.

If the generated $O_2$ variation index trend is less than the predetermined baseline value 210 for the predetermined time period, i.e., the generated $O_2$ variation index trend is sustained, the secondary confirmation process confirms the identification of the malignant cardiac event, and therapy is delivered, Block 512.

According to an embodiment of the present invention, the deviation threshold of Block 505 is determined, for example, by periodically computing $O_2$ variation indexes using Equation 1 and generating a corresponding oxygen variation index trend during a known period of motion-free normal sinus rhythm, such as while the patient is sleeping. The deviation of the oxygen variation indexes generated during normal sinus rhythm from the corresponding oxygen variation index trend generated for the sample collection period is then determined using the same process utilized in Block 503, such as the mean square deviation, for example. Other methods for determining the deviation may be utilized rather than the mean square deviations, such as the mean of absolute values of deviations, for example. The deviation threshold utilized for Block 505 is then updated by being set equal to the deviation of the oxygen variation indexes from the trends generated during motion-free normal sinus rhythm, or to a multiple or a fraction of the deviation.

Figure 8:
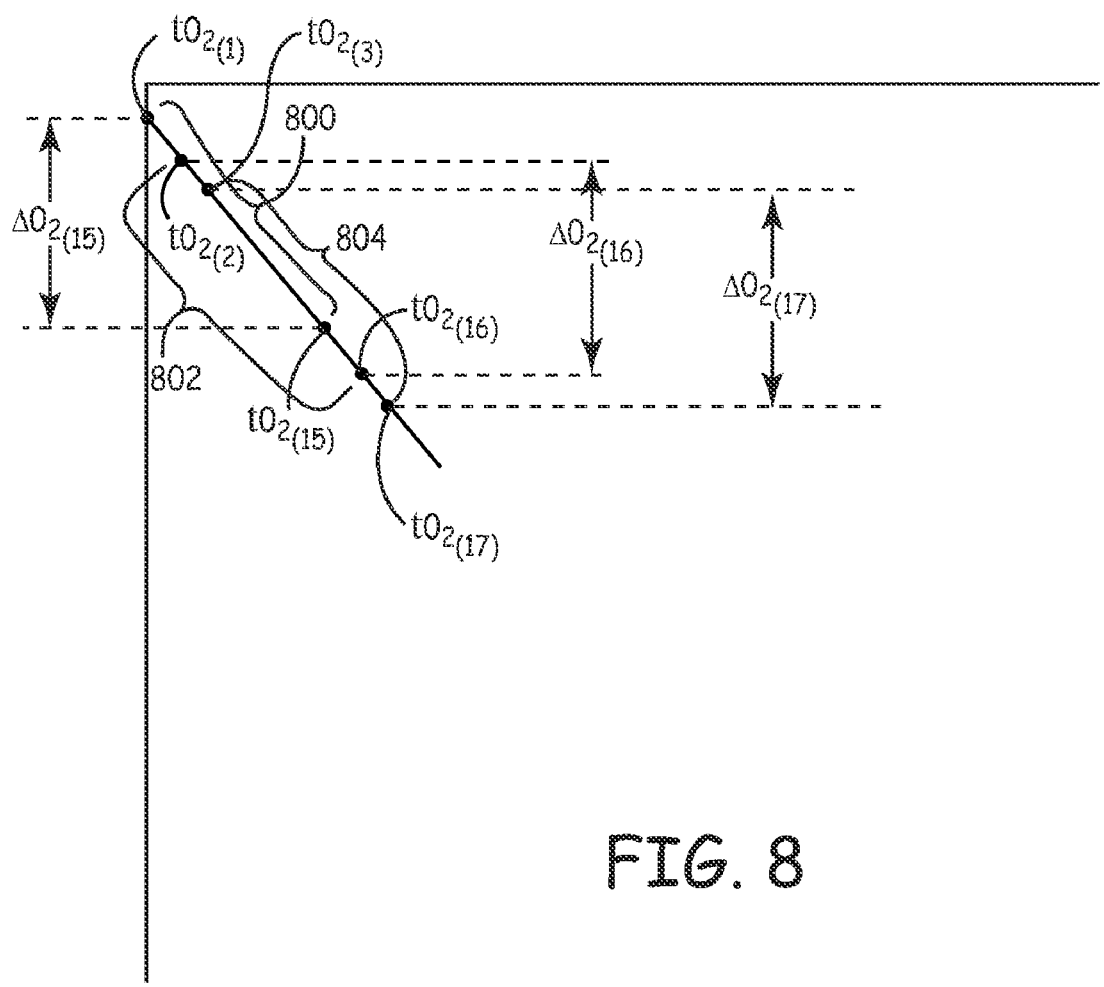
FIG. 8 is an exemplary graphical representation of an $O_2$ variation index trend utilized in a method of delivering a therapy in a medical device according to an embodiment of the present invention.

FIG. 8 is an exemplary graphical representation of an $O_2$ variation index trend utilized in a method of delivering a therapy in a medical device according to an embodiment of the present invention. According to an embodiment of the present invention, during the incrementing of the corrected $O_2$ variation index trend, Block 508, the endpoints of the current determined $O_2$ variation index trends are used to calculate a current trend value $\Delta O_{2(n)}$ associated with the current sample collection period. For example, as illustrated in FIG. 8, once the $O_2$ variation index trend 800 has been determined, and the first and the last $O_2$ variation index samples of the 15 $O_2$ variation index samples associated with the window of $O_2$ variation indexes 600 are projected onto the $O_2$ variation index trend 800 to determine a first index trend $tO_{2(1)}$ and a last index trend $tO_{2(15)}$ associated with the $O_2$ variation index trend 800, as described above, the change in index trend $\Delta O_{2(15)}$ for the $O_2$ variation index trend 800 is then determined as the difference between the first $O_2$ variation index trend $tO_{2(1)}$ and the last $O_2$ variation index trend $tO_{2(15)}$, i.e., $tO_{2(15)} - tO_{2(1)}$. The corrected $O_2$ variation index trend $cO_2$ is then set equal to the determined change in the index trend $\Delta O_{2(15)}$.

A next $O_2$ variation index trend 802 is then determined for the subsequent window of $O_2$ variation index samples, i.e., the next $O_2$ variation index sample $O_{2(16)}$ and the previous n−1 of the $O_2$ variation index samples $O_{2(2)}$ through $O_{2(15)}$. The first and the last $O_2$ variation index samples $O_{2(2)}$ and $O_{2(16)}$ are then projected onto the $O_2$ variation index trend 802 to determine a first index trend $tO_{2(2)}$ and a last index trend $tO_{2(16)}$ associated with the $O_2$ variation index trend 802, and the change in the index trend $\Delta O_{2(16)}$ for the $O_2$ variation index trend 802 is then determined as the difference between the first index trend $tO_{2(2)}$ and the last index trend $tO_{2(16)}$, i.e., $tO_{2(16)} - tO_{2(2)}$.

The corrected $O_2$ variation index trend $cO_2$ is then incremented in Block 508 by being set equal to the sum of the previous corrected $O_2$ variation index trend and the product of the inverse of the number of samples in the window of $O_2$ variation indexes and the determined change in the $O_2$ variation index trend $\Delta O_{2(16)}$ for the $O_2$ variation index trend 800 for the current window of $O_2$ variation index samples. This process is then repeated so that during noise free periods identified in Block 505, the corrected $O_2$ variation index trend $cO_{2(i)}$ is incremented for each window of $O_2$ variation index samples by being set equal to the sum of the previous corrected $O_2$ variation index trend $cO_{2(i-1)}$ and the product of the inverse of the number of samples n in the sample collection period and the determined change in the $O_2$ variation index trend $\Delta O_{2(i)}$ for the $O_2$ variation index trend associated with the current window of $O_2$ variation index samples, indicated by the following equation:

$$cO_{2(i)} = cO_{2(i-1)} + 1/n(\Delta O_{2(i)}) \qquad \text{Equation 2}$$

According to another embodiment of the present invention, once the first sample collection period, such as 0-5 seconds for example, has expired and the corresponding $O_2$ variation index trend 800 has been determined, 15 $O_2$ variation index trend values $tO_{2(1)}$ through $tO_{2(15)}$ along the $O_2$ variation index trend 800 are identified by projecting the location of each of the 15 $O_2$ variation index samples for the sample collection period onto the $O_2$ variation index trend 800. The change in the $O_2$ variation index trend $\Delta O_{2(15)}$ for the $O_2$ variation index trend 800 is then determined as the difference between the first index trend $tO_{2(1)}$ and the last index trend $tO_{2(15)}$, i.e., $tO_{2(15)} - tO_{2(1)}$.

An $O_2$ variation index trend 802 is then determined for the next window of $O_2$ variation index samples, and corresponding trend values $tO_{2(2-16)}$ along the $O_2$ variation index trend 802 are determined by projecting the location of each of the $O_2$ variation index samples onto the $O_2$ variation index trend 802 as described above. The change in the $O_2$ variation index trend $\Delta O_{2(16)}$ for the $O_2$ variation index trend 802 is then determined as the difference between the first index trend $tO_{2(2)}$ and the last index trend $tO_{2(16)}$, i.e., $tO_{2(16)} - tO_{2(2)}$. The corrected $O_2$ variation index trend is then incremented by being set equal to the sum of the change in the current $O_2$ variation index trend $\Delta O_{2(16)}$ and the product of the inverse of the number of samples n in window of $O_2$ variation indexes and the change in the $O_2$ variation index trend $\Delta O_{2(15)}$ determined for the previous sample collection period, indicated by the equation $cO_{2(16)} = 1/n(\Delta O_{2(15)}) + \Delta O_{2(16)}$.

An $O_2$ variation index trend 804 is then determined for the next window of $O_2$ variation index samples, and corresponding trend values $tO_{2(3-17)}$ along the $O_2$ variation index trend 804 are determined by projecting the location of each of the $O_2$ variation index samples associated with the window onto the $O_2$ variation index trend 804. The change in the $O_2$ variation index trend $\Delta O_{2(17)}$ for the $O_2$ variation index trend 804 is then determined as the difference between the first $O_2$ variation index trend $tO_{2(3)}$ and the last $O_2$ variation index trend $tO_{2(17)}$, i.e., $tO_{2(17)}-tO_{2(3)}$. The corrected $O_2$ variation index trend $cO_{2(17)}$ is then incremented by being set equal to the sum of the product of the inverse of the number of samples n in the sample collection period and the change in the $O_2$ variation index trend $\Delta O_{2(15)}$ determined for the first $O_2$ variation index trend 800, the product of the inverse of the number of samples n in the sample collection period and the change in the $O_2$ variation index trend $\Delta O_{2(16)}$ determined for the previous $O_2$ variation index trend 802 and the change in the $O_2$ variation index trend $\Delta O_{2(17)}$ for the current $O_2$ variation index trend 804, indicated by the equation: $cO_{2(17)}=1/n(\Delta O_{2(15)})+1/n(\Delta O_{2(16)})+\Delta O_{2(17)}$.

Once the corrected $O_2$ variation index trend for three noise free sample collections have been determined, an initialization period for the corrected $O_2$ variation index trend incrementation in Block 508 is completed, and the corrected $O_2$ variation index trend $cO_2$ is updated for subsequent windows of $O_2$ variation index samples identified by the determined value of the last $O_2$ variation index trend corresponding to the endpoint of the most recent determined $O_2$ variation index trend using the following equation:

$$cO_{2(i+n)}=cO_{2(i+n-2)}+1/n(\Delta O_{2(i+n-1)})+\Delta O_{2(i+n)} \qquad \text{Equation 3}$$

where i is the last $O_2$ variation index trend corresponding to the endpoint of the most recent determined $O_2$ variation index trend, $cO_{2(i+n-2)}$ is the corrected $O_2$ variation index trend associated with the window of $O_2$ variation index samples occurring two sample collection periods prior to the current window of $O_2$ variation index samples, 1/n is the inverse of the number of samples n in the sample collection period, $(\Delta O_{2(i+n-1)})$ is the corrected $O_2$ variation index trend associated with the window of $O_2$ variation index samples occurring one sample collection period prior to the current window of $O_2$ variation index samples, and $\Delta O_{2(i+n)}$ is the change in the current $O_2$ variation index trend.

In both embodiments of the present invention associated with Equations 2 and 3, since the corrected $O_2$ variation index trend is incremented only for those sample collection periods that are determined to be noise free, Yes in Block 505, the present invention accounts for those periods when the $O_2$ variation indexes are likely associated with noise and adjusts the total $O_2$ variation index trend accordingly by not incrementing the corrected $O_2$ variation index trend when noise is likely, i.e., when the deviation is not less than the deviation threshold, No in Block 505.

Figure 9:
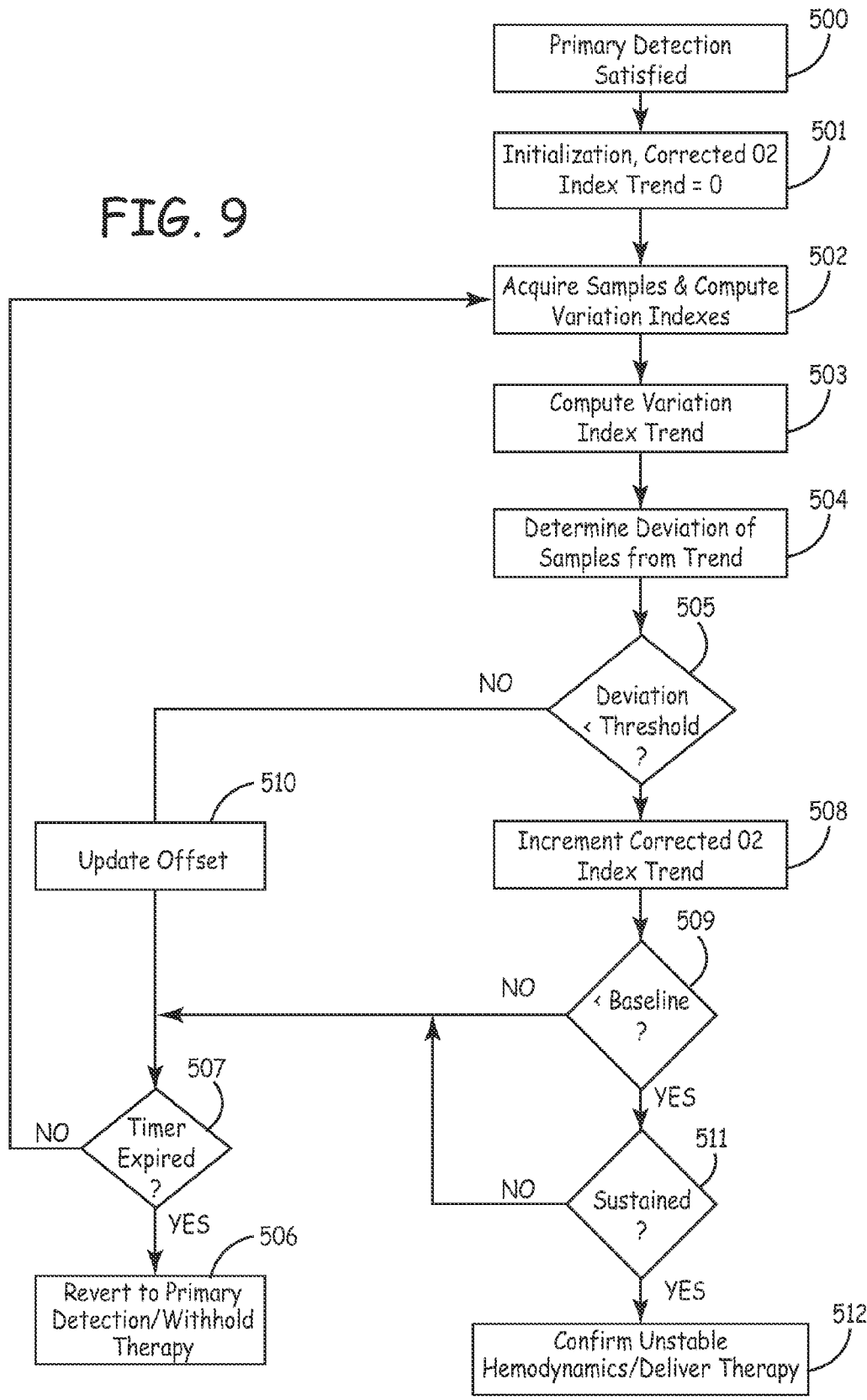
FIG. 9 is a flow chart of a method of delivering a therapy in a medical device according to an embodiment of the present invention.
Figure 10:
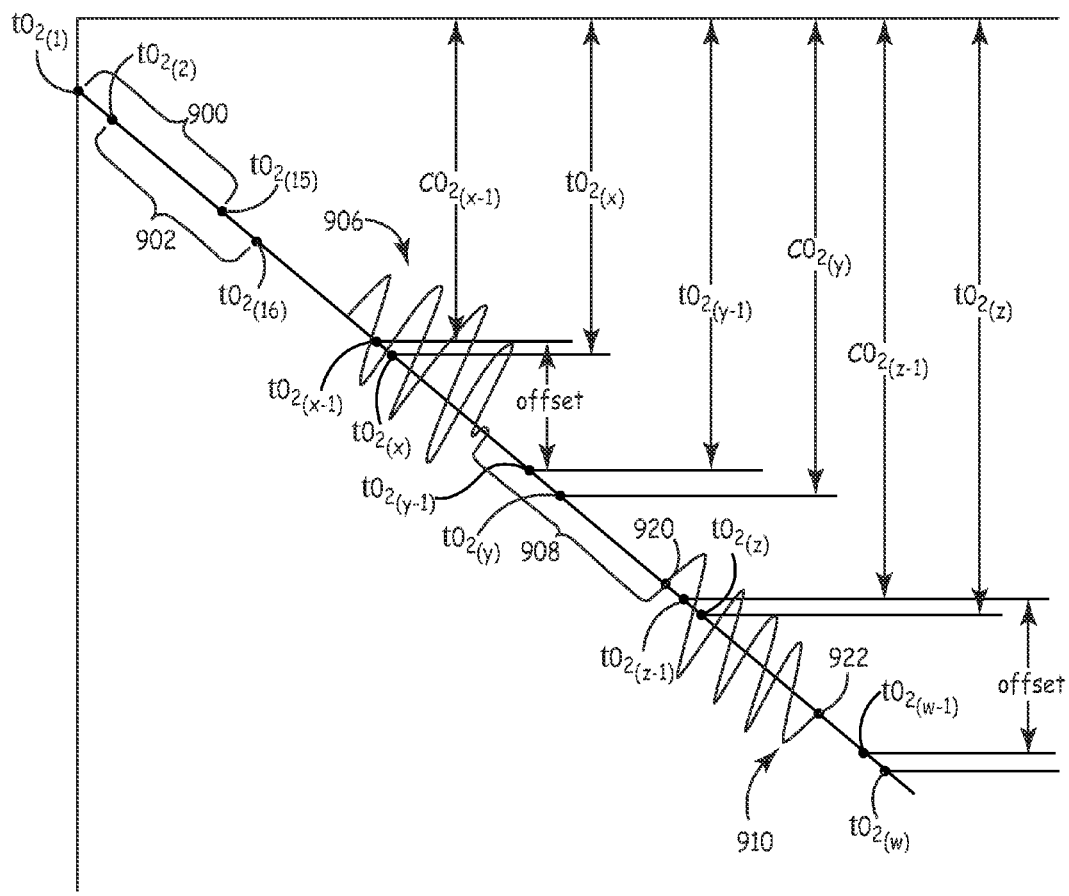
FIG. 10 is an exemplary graphical representation of an $O_2$ variation index trend utilized in a method of delivering a therapy in a medical device according to an embodiment of the present invention.

FIG. 9 is a flow chart of a method of delivering a therapy in a medical device according to an embodiment of the present invention. FIG. 10 is an exemplary graphical representation of an $O_2$ variation index trend utilized in a method of delivering a therapy in a medical device according to an embodiment of the present invention. As illustrated in FIGS. 9 and 10, according to an embodiment of the present invention, once the first sample collection period, i.e., 0-5 seconds, has expired, and therefore both the associated $O_2$ variation index trend 900, Block 503, and the deviation of the associated samples from the trend, Block 504, over that period have been determined and utilized to determine that the sample is likely to be noise free, Yes in Block 505, the last trend value $tO_{2(15)}$ along the corresponding $O_2$ variation index trend 900 is determined by projecting the location of the last $O_2$ variation index sample of the window $O_{2(1-15)}$ onto the $O_2$ variation index trend 900.

For the initial sample collection period, the corrected $O_2$ variation index trend $cO_2$ is incremented in Block 508 by being set equal to the last trended value $tO_{2(15)}$, which is then utilized as the generated corrected $O_2$ variation index trend $cO_2$ for the determination of Block 509.

The window of $O_2$ variation index samples shifts to include the next $O_2$ variation index sample $O_{2(16)}$ and the previous n−1 $O_2$ variation index samples $O_{2(2-15)}$ from the previous window of samples. The current $O_2$ variation index samples $O_{2(2-16)}$ are then used to determine the next $O_2$ variation index trend 902, with the value of the last $O_2$ variation index sample $O_{2(16)}$ being projected onto the current $O_2$ variation index trend 902 to generate a corresponding last trended value $tO_{2(16)}$, which is then utilized as the corrected $O_2$ variation index trend in the determination of Block 509, and so forth. An $O_2$ variation index trend is then determined for the next window of $O_2$ variation index samples and the corresponding last trended value is determined by projecting the location of the last or most recent $O_2$ variation index sample onto the $O_2$ variation index trend, and so forth.

The process continues as described on a sample by sample basis until the effects of noise cause the $O_2$ variation index samples to deviate from the $O_2$ variation index trend so that the deviation becomes greater than the deviation threshold, No in Block 505. Once the deviation of the $O_2$ variation indexes is determined not to be less than the deviation threshold, indicating a likelihood that the determined cardiac event is the result of noise, a corrected $O_2$ variation index offset, which operates to keep a running account of the non-noise free periods, is updated, Block 510. In particular, as the window of $O_2$ variation index samples continues to be shifted to include a next $O_2$ variation index sample and the previous n−1 samples, and the corrected $O_2$ variation index trend continues to be updated accordingly, the leading edge of the window of $O_2$ variation index samples may begin to advance within a noise portion 906. Once the window of $O_2$ variation index samples advances far enough within the noise portion 906, the deviation of the samples in the current sample window will become greater than the deviation threshold, No in Block 505, and therefore the value of the corrected $O_2$ variation index trend is held equal to the last corrected $O_2$ variation index trend that was not associated with noise.

Assuming that the window of $O_2$ variation index samples that initially deviates from the corresponding $O_2$ variation index trend to be indicative of noise occurs at $O_2$ variation index sample $O_{2(x)}$, which corresponds to trended $O_2$ variation index sample $tO_{2(x)}$, and the corrected $O_2$ variation index is therefore no longer updated, the offset is updated in Block 510 by being set equal to the difference between the current trended $O_2$ variation index $tO_{2(x)}$ and the corrected $O_2$ variation index associated with the last window of samples determined to be noise free, illustrated in FIG. 10 by $tO_{2(x)}-cO_{2(x-1)}$. The updating of the offset continues, with the offset being updated in Block 510 for each subsequent window of samples by continuing to determine the difference between the current trended $O_2$ variation index $tO_{2(x+m)}$ and the corrected $O_2$ variation index associated with the last window of samples determined to be noise free, until another window of noise free $O_2$ variation index samples is received, Yes in Block 505. The updating of the offset in Block 510 as the window of samples advances during detection of the noise 906 can therefore be summarized generally by the following equation:

$$\text{offset}=tO_{2(i+m)}-cO_{2(i-1)} \qquad \text{Equation 4}$$

where i is the first instance that noise is detected for a given noise period, m is the subsequent consecutive samples during this period of noise, and i−1 corresponds to the last corrected $O_2$ variation index trend value for which the associated window of samples was determined to be noise free immediately prior to the trend value for which the associated window of samples was determined to be likely corrupted by noise.

Assuming the next noise free $O_2$ variation index sample is received for the $O_2$ variation index sample associated with $O_2$ variation index trend $tO_{2(y)}$, for example, the incrementing of the corrected $O_2$ variation index trend in Block 508 then continues and the updating of the offset in Block 510 is suspended. As a result, the offset was last updated for the previous sample $O_{2(y-1)}$ by being set equal to the difference between the value of the $O_2$ variation index trend $tO_{2(y-1)}$ generated during the window of samples occurring just prior to the initial noise free window of samples and the value of the corrected $O_2$ variation index $cO_{2(x-1)}$ associated with the last window of samples determined to be noise free.

The corrected $O_2$ variation index trend is then incremented in Block 508 by the difference between the current noise free trend value $tO_{2(y)}$ and the sum of previously determined offsets, which in the example would be the offset associated with noise period 906, illustrated by $tO_{2(y-1)} - cO_{2(x-1)}$. It may also be noted that since noise period 906 is the first noisy period in the example, the offset equals the total change in the $O_2$ variation index trend during the period of noise $tO_{2(y-1)} - cO_{2(x-1)}$. The incrementing of the corrected $O_2$ variation index trend continues with the window of $O_2$ variation index samples being shifted to include the next $O_2$ variation index sample $O_{2(y+m)}$ and the previous 14 $O_2$ variation index samples starting from $O_2$ variation index sample $O_{2(y+m-14)}$, so that the subsequent windows of samples are used to determine the next $O_2$ variation index trends, and the last $O_2$ variation index sample $O_{2(y+m)}$ is projected onto the current $O_2$ variation index trend to generate a corresponding trend value $tO_{2(y+m)}$. The corrected $O_2$ variation index trend is then incremented in Block 508 by subtracting the offset updated during the previous noise period 906 from the current trend value $tO_{2(y+m)}$.

Assuming, for example, that the current window of $O_2$ variation index samples subsequently remains noise free for a noise free period of time 908 and then deviates from the corresponding $O_2$ variation index trend, No in Block 505, to be indicative of a next noise portion 910 at $O_2$ variation index sample $O_{2(z)}$, which corresponds to trended $O_2$ variation index sample $tO_{2(z)}$, the corrected $O_2$ variation index is no longer incremented for trended $O_2$ variation index sample $tO_{2(z)}$, while the offset is updated in Block 510 by being set equal to the difference between the current value of the non-noise free trended $O_2$ variation index sample $tO_{2(z)}$ and the value of the corrected $O_2$ variation index associated with the last window of samples determined to be noise free, i.e. $cO_{2(z-1)}$. The updating of the offset continues for each subsequent window of samples by taking the difference between the value of the trended $O_2$ variation index generated for the current non-noise free window of samples and the value of the corrected $O_2$ variation index associated with the last window of samples determined to be noise free, until the next noise free $O_2$ variation index sample is received.

For example, assuming the next noise free $O_2$ variation index sample is received for the $O_2$ variation index sample associated with trended $O_2$ variation index sample $tO_{2(w)}$, the incrementing of the corrected $O_2$ variation index trend in Block 508 then continues and updating of the offset in Block 510 is suspended. As a result, the offset was last updated for the previous sample $tO_{2(w-1)}$ by being set equal to the difference between the value of the $O_2$ variation index trend $tO_{2(w-1)}$ generated during the window of samples occurring just prior to the initial noise free window of samples and the value of the corrected $O_2$ variation index associated with the last window of samples determined to be noise free, $cO_{2(z-1)}$. It should be noted that the offset at this point equals the sum of the changes observed during the two preceding noisy periods 906 and 910, $[tO_{2(w-1)} - tO_{2(z-1)}] + [tO_{2(y-1)} - tO_{2(x-1)}]$.

The corrected $O_2$ variation index trend is then computed as the difference between the current noise free $O_2$ variation index trend value $tO_{2(w)}$ and the current offset. In this way, the corrected $O_2$ variation index trend is updated for subsequent windows of $O_2$ variation index samples by subtracting the sum of the previous changes in the $O_2$ variation index trend values associated with noise from the current $O_2$ variation index trend value, described generally by the following equation:

$$cO_{2(i-n+1)} = tO_{2(i-n+1)} - \Sigma \text{offset} \qquad \text{Equation 5}$$

where i is the current $O_2$ variation index trend value and n is the number of samples in a sampling window. $\Sigma$offset represents the current offset at any point in time, where the summation, $\Sigma$, is indicative of the fact that the current offset represents the sum of individual offsets accumulated during each individual period of noise since the start of the flow chart As can be seen in Equation 5, the incrementing of the corrected $O_2$ variation index trend does not begin until the first n samples associated with the first window of samples 900 are received.

As illustrated in FIG. 10, each period of noise 906, 910 associated with the $O_2$ variation index trend includes a start point 920 and an endpoint 922. Ideally, noise will be detected, No in Block 505, when the endpoint of the associated $O_2$ variation index trend is located at or just beyond the start point 920 of the period of noise 906, 910, and will subsequently no longer be detected, Yes in Block 505, when the subsequent endpoint of the associated $O_2$ variation index trend is located at or just beyond the endpoint 922. However, as can be in the embodiment described above in reference to FIG. 10, when the endpoints of the $O_2$ variation index trends are used in the determination of both the incrementing of the corrected $O_2$ variation index trend, Block 508, and the updating of the offset, Block 510, the window of $O_2$ variation index samples will be located beyond the start point 920 and within the noise portion when the noise is initially identified, No in Block 505, and beyond the endpoint 922 and outside the noise period when noise is subsequently no longer detected, Yes in Block 505.

According to an embodiment of the present invention, therefore, in order to increase the likelihood that the offset will correspond to the actual period of noise, the present invention utilizes a predetermined trend value other than the leading endpoint of the $O_2$ variation index trend. Rather than projecting on the first and the last sample of each of the n samples in the samples of windows to obtain the first $O_2$ variation index trend value and the last $O_2$ variation index trend value for each generated $O_2$ variation index trend as described above, each sample within the window of samples is projected onto the $O_2$ variation index trend to generate n $O_2$ variation index trend values so that any one of the trend values can then be utilized during the incrementing and updating of the corrected $O_2$ variation index trend and the offset, respectively.

For example, once the initial $O_2$ variation index trend 900 has been computed, Block 503 and the deviation of the samples from the $O_2$ variation index trend 900 has been determined, Block 504, resulting in a determination that the sample is not likely associated with noise, Yes in Block 505, the corrected $O_2$ variation index trend $cO_2$ is incremented in Block 508 by being set equal to a predetermined one of the 15 trend values located between the first trend value $tO_{2(1)}$ associated with the first $O_2$ variation index sample of the window and the last trend value $tO_{2(15)}$ associated with the last $O_2$ variation index sample of the window $O_{2(15)}$. According to an embodiment of the present invention, the corrected $O_2$ variation index trend $cO_2$ is incremented by being set equal to the central trend value, i.e., $O_2$ variation index trend value $tO_{2(8)}$.

The process continues with the window of $O_2$ variation index samples being shifted to include the next $O_2$ variation index sample $O_{2(16)}$ and the previous 14 $O_2$ variation index samples from the previous window of samples $O_{2(2)}$ through $O_{2(15)}$. The current window of samples $O_{2(2-16)}$ is then used to determine the next $O_2$ variation index trend 902, and the central $O_2$ variation index sample $O_{2(9)}$ is projected onto the current $O_2$ variation index trend 902 to generate a corresponding central trend value $tO_{2(9)}$. The corrected $O_2$ variation index trend is then incremented in Block 508 by being set equal to the central trend value $tO_{2(8)}$. The process continues as described above using the predetermined trend value in place of the last $O_2$ variation index trend value to perform the incrementing and updating of the corrected $O_2$ variation index trend and the offset, respectively.

Figure 11:
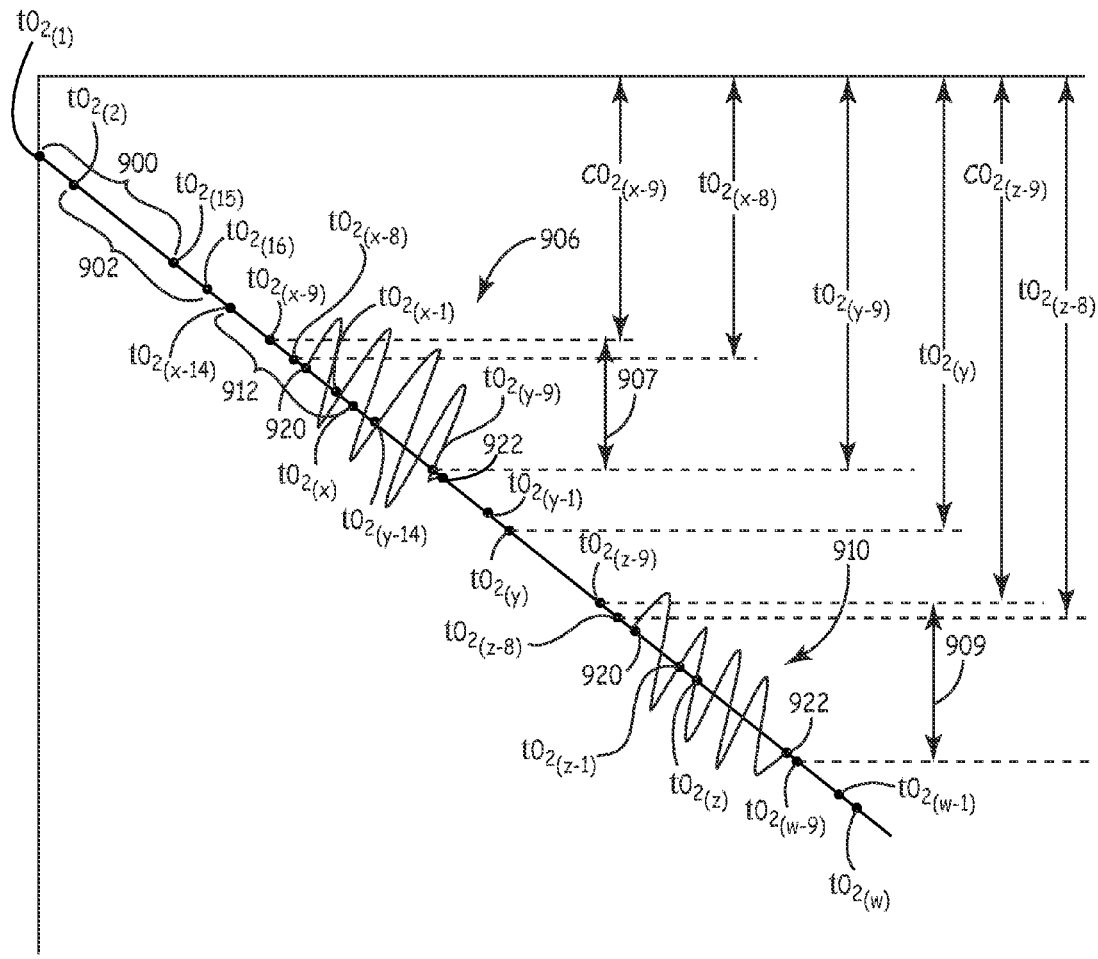
FIG. 11 is an exemplary graphical representation of generation of a corrected $O_2$ variation index trend offset utilized in a method of delivering a therapy in a medical device according to an embodiment of the present invention.

FIG. 11 is an exemplary graphical representation of generation of a corrected $O_2$ variation index trend offset utilized in a method of delivering a therapy in a medical device according to an embodiment of the present invention. According to another embodiment of the present invention, rather than using a single trended value during the incrementing and updating of the corrected $O_2$ variation index trend and the offset, respectively, multiple values may be utilized. For example, as illustrated in FIG. 11, the last or leading end $O_2$ variation index trend is utilized during the incrementing of the $O_2$ variation index trend and a predetermined $O_2$ variation index trend value is utilized during the updating of the offset. The predetermined $O_2$ variation index trend value is chosen to increase the likelihood that the offset will correspond to the actual period of noise, such as the midpoint of the $O_2$ variation index trend, for example. In this way, the incrementing of the corrected $O_2$ variation index trend is performed using the leading endpoint of the determined $O_2$ variation index trend during the initial noise free period associated with $O_2$ variation index trends 900, 902, and so forth, and the process continues as described on a sample by sample basis until the effects of noise cause the $O_2$ variation index samples to deviate from the $O_2$ variation index trend, No in Block 505.

Assuming again that the window of $O_2$ variation index samples that initially deviates from the corresponding $O_2$ variation index trend to be indicative of noise occurs at $O_2$ variation index sample $O_{2(x)}$, which corresponds to $O_2$ variation index trend $tO_{2(x)}$, incrementing of the corrected $O_2$ variation index is therefore suspended. It should be noted that while computing an offset in Block 510, the corrected $O_2$ variation index trend values belong to the immediately prior sampling window. During the updating of the offset in Block 510, the $O_2$ variation index trend offset is updated by determining the difference between the leading $O_2$ variation index trend value $tO_{2(x-8)}$ of the current noise corrupted $O_2$ variation index trend $tO_{2(x)}$ and the corrected $O_2$ variation index trend $cO_{2(x-9)}$ determined immediately prior to the central $O_2$ variation index trend $tO_{2(x-8)}$.

The process continues for subsequent windows of samples, with the determination of whether the current window of samples are corrupted by noise being made in Block 505 and the updating of the offset in Block 510 being made based on the predetermined trend value, until the next noise free $O_2$ variation index sample is identified, Yes in Block 505, so that the offset is updated for each window of samples as set forth generally by the following equation:

$$\text{offset} = tO_{2(i+m-d)} - cO_{2(i-1)} \qquad \text{Equation 6}$$

where i is the first instance that noise is detected for a given noise period, m is the next sample, d corresponds to the predetermined trend value associated with the current noise corrupted window of $O_2$ variation index samples, and i−1 corresponds to the immediate last trend value associated with the window of samples determined to be noise free prior to the predetermined trend value associated with the current noise corrupted window of samples.

For example, if the next noise free $O_2$ variation index sample is received at $O_2$ variation index trend $tO_{2(y)}$, the offset was therefore last updated during the previous trended $O_2$ variation index sample $tO_{2(y-1)}$ by being set equal to the difference between the central $O_2$ variation index trend value $tO_{2(y-9)}$ of the current noise corrupted $O_2$ variation index trend and the corrected $O_2$ variation index trend $cO_{2(x-9)}$ determined prior to the central $O_2$ variation index trend $tO_{2(x-8)}$. Incrementing of the corrected $O_2$ variation index trend $cO_{2(y)}$ is resumed in Block 508 by subtracting the offset 907 from the current $O_2$ variation index trend $tO_{2(y)}$.

The process continues during over m windows of $O_2$ variation index samples occurring over the subsequent noise free portion 908, with the corrected $O_2$ variation index being incremented, Block 508, by subtracting the offset 907 from the current trend value $tO_{2(y+m)}$. Assuming, for example, that the current window of $O_2$ variation index samples subsequently remains noise free for a period of time associated with the noise free period 908 and then deviates from the corresponding $O_2$ variation index trend, No in Block 505, to be indicative of a next noise portion 910 at $O_2$ variation index trend $tO_{2(z)}$, incrementing of the corrected $O_2$ variation index is therefore suspended and updating of the offset in Block 510 resumes.

During the updating of the offset, the $O_2$ variation index trend offset is updated by determining the difference between the central $O_2$ variation index trend value $tO_{2(z-8)}$ of the current noise corrupted $O_2$ variation index trend $tO_{2(z)}$ and the corrected $O_2$ variation index trend $cO_{2(z-9)}$ determined immediately prior to the central $O_2$ variation index trend $tO_{2(z-8)}$. The process continues for subsequent windows of samples, with the determination of whether the current window of samples are corrupted by noise being made in Block 505 and the updating of the offset in Block 510 being made based on the predetermined trend value using Equation 6, as in the previous noise period 906 until the next noise free $O_2$ variation index sample is identified, Yes in Block 505.

For example, if the next noise free $O_2$ variation index sample is received at $O_2$ variation index trend $tO_{2(w)}$, the offset was therefore last updated for the previous $O_2$ variation index trend $tO_{2(w-1)}$ by being set equal to the difference between the central $O_2$ variation index trend $tO_{2(w-9)}$ associated with the previous $O_2$ variation index trend and the last incremented corrected $O_2$ variation index trend $cO_{2(z-9)}$ prior to the central $O_2$ variation index trend $cO_{2(w-9)}$. Incrementing of the corrected $O_2$ variation index trend $cO_{2(w)}$ is resumed in Block 508 by subtracting the sum of the offsets 907 and 909 from the current $O_2$ variation index trend $tO_{2(w)}$.

The process continues during over m windows of $O_2$ variation index samples occurring over the subsequent noise corrupted and noise free portions, with the offset being updated by determining the current offset using Equation 6 and the incrementing of the corrected $O_2$ variation index in Block 508 being performed by subtracting the sum of the prior determined offsets from the current $O_2$ variation index trend, set forth generally in Equation 5 above.

Figure 12:
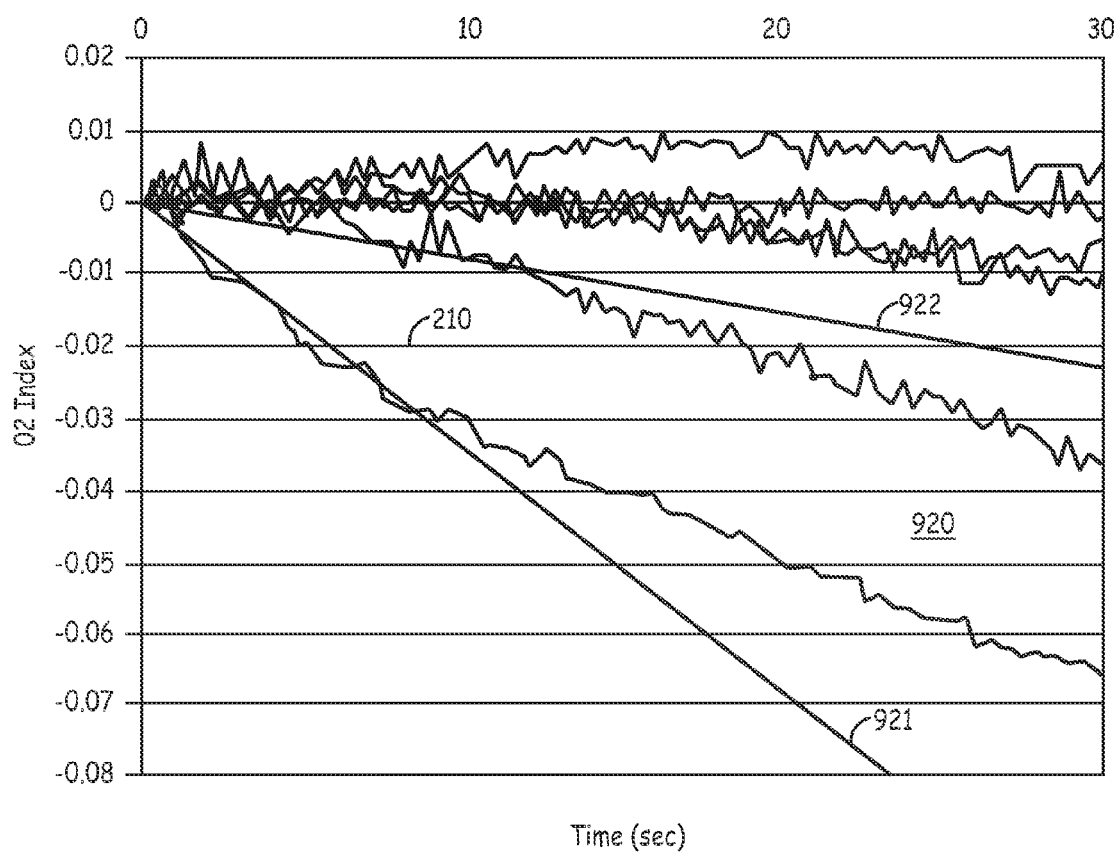
FIG. 12 is an exemplary graphical representation of an $O_2$ variation index trend utilized in a method of delivering a therapy in a medical device according to an embodiment of the present invention.
Figure 13:
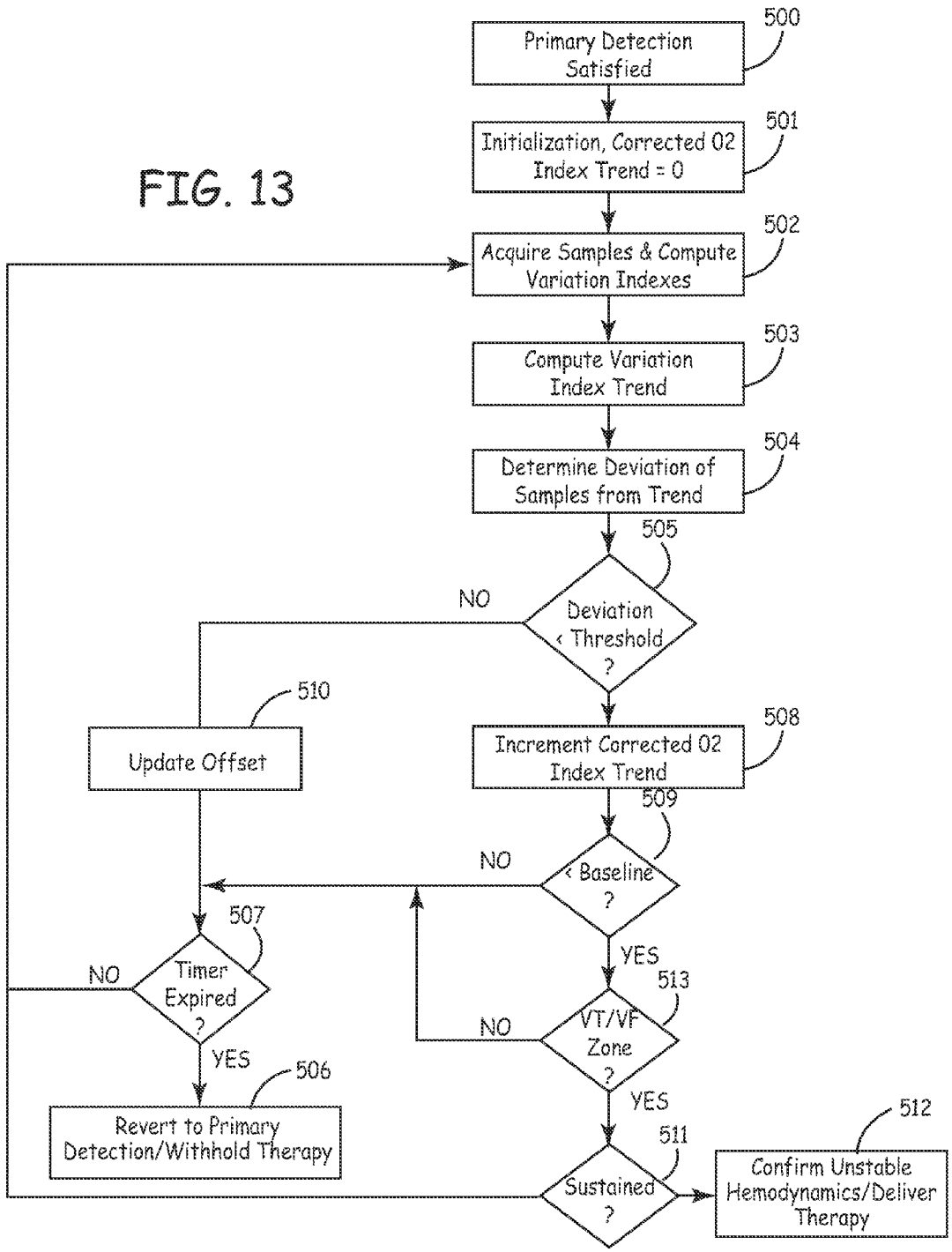
FIG. 13 is a flow chart of a method of delivering a therapy in a medical device according to an embodiment of the present invention.

FIG. 12 is an exemplary graphical representation of an $O_2$ variation index trend utilized in a method of delivering a therapy in a medical device according to an embodiment of the present invention. FIG. 13 is a flow chart of a method of delivering a therapy in a medical device according to an embodiment of the present invention. As illustrated in FIGS. 12 and 13, according to an embodiment of the present invention, a zone 920 for identifying when the event is most likely associated with an unstable hemodynamic event, such as ventricular tachycardia or ventricular fibrillation, is defined based on a non-physiologic event threshold 921 and a normal sinus rhythm threshold limit 922, so that once the $O_2$ variation index trend is determined to be less than the baseline value 210, a determination is made as to whether the $O_2$ variation index trend is within the VT/VF zone 920, Block 513.

In particular, for example, a determination is made as to whether the slope of the $O_2$ variation index trend, determined based on two of the known trended values of the $O_2$ variation index trend, such as the first and the last trended value, for example, is either greater than the slope of threshold 921 or less than the slope of threshold 922, and therefore outside the VT/VF zone 920, Block 513. If the $O_2$ variation index trend is determined to be outside the VT/VF zone, No in Block 513, the current stored slope values are cleared and the determination as to whether the episode verification time period has expired is made, Block 507, described above. If the $O_2$ variation index trend is determined to be within the VT/VF zone, Yes in Block 513, a determination is made as to whether the $O_2$ variation index trend is sustained, i.e., remains within the zone 920 for a predetermined time period, such as over six samples or two seconds, for example, Block 515.

If the $O_2$ variation index trend is not sustained, the process returns to Block 502 so that the deviation of the $O_2$ variation index samples from the $O_2$ variation index trend, Blocks 503 and 504 is determined for the next window of $O_2$ variation index samples, described above. If the $O_2$ variation index trend is sustained within the VT/VF zone 920 for the predetermined period of time, the secondary confirmation process confirms the identification of the malignant cardiac event, and therapy is delivered, Block 512, and the current stored slope values are cleared.

Both threshold 921, which corresponds to abrupt changes in the slope of the $O_2$ variation index trend indicative of non-physiological events, such as a change in posture for example, and threshold 922, which corresponds to normal sinus rhythm, are programmable. According to an exemplary embodiment of the present invention, threshold 921 corresponds to the $O_2$ variation index trend crossing the baseline value 210 in five seconds or less, so that threshold 921 corresponds to a slope of 0.004 (i.e., 0.02 divided by 5 seconds), and threshold 922 corresponds to the $O_2$ variation index trend crossing the baseline value 210 in 20 or more seconds, so that threshold 922 corresponds to a slope of 0.001 (i.e., 0.02 divided by 20 seconds).

Figure 14:
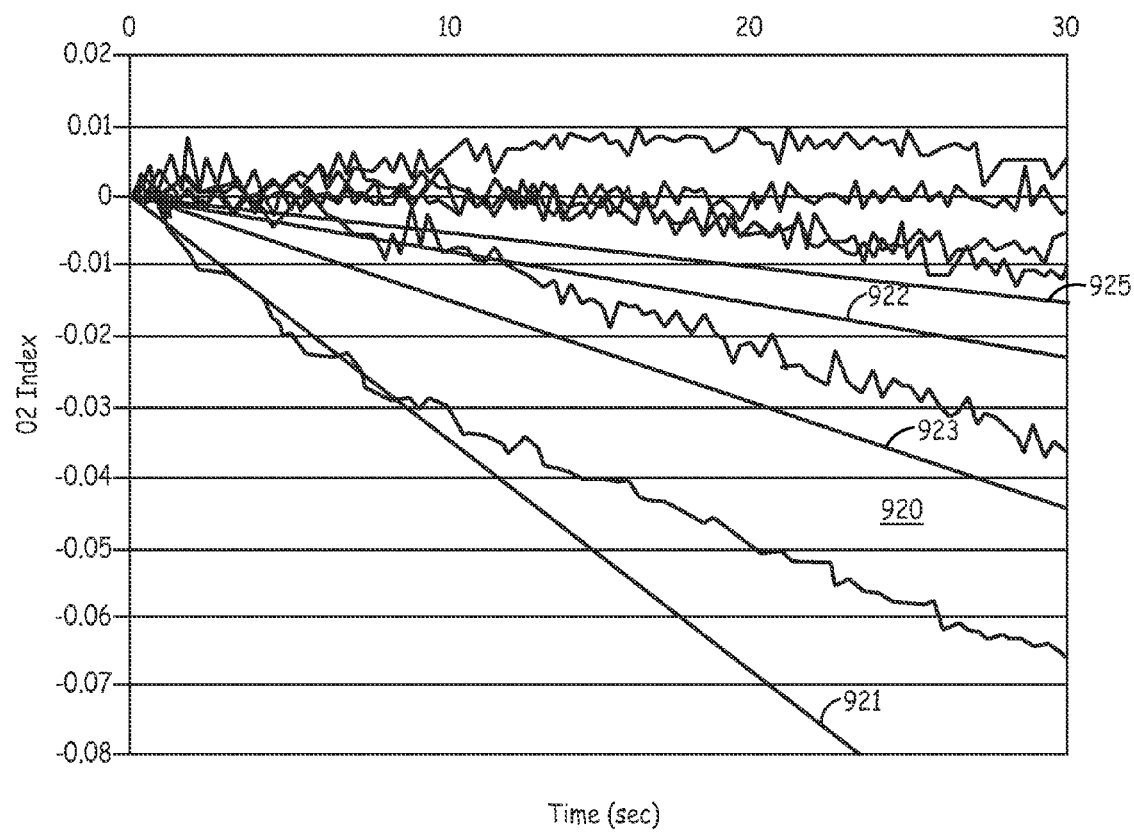
FIG. 14 is an exemplary graphical representation of an $O_2$ variation index trend utilized in a method of delivering a therapy in a medical device according to an embodiment of the present invention.
Figure 15:
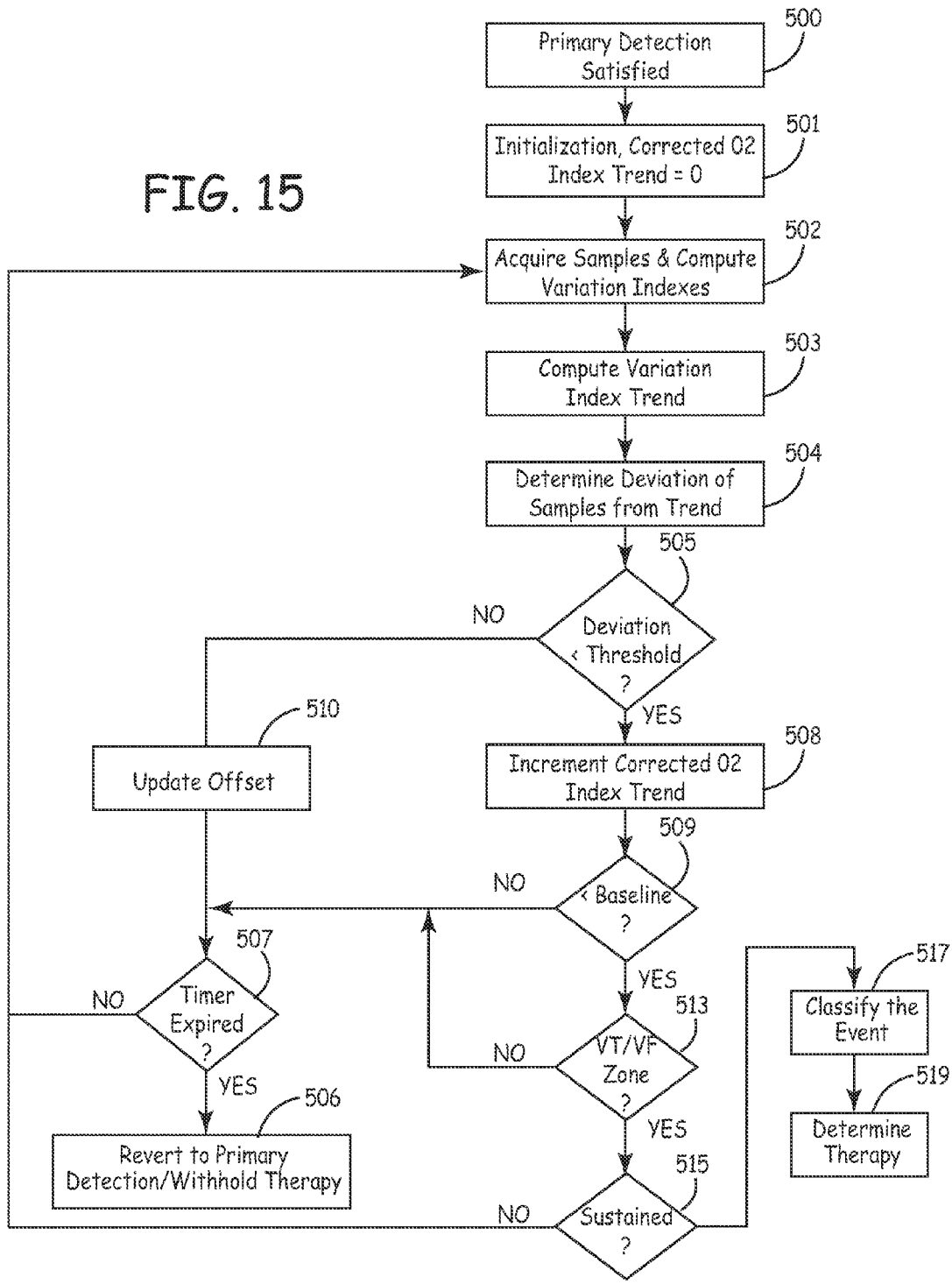
FIG. 15 is a flow chart of a method of delivering a therapy in a medical device according to an embodiment of the present invention.

FIG. 14 is an exemplary graphical representation of an $O_2$ variation index trend utilized in a method of delivering a therapy in a medical device according to an embodiment of the present invention. FIG. 15 is a flow chart of a method of delivering a therapy in a medical device according to an embodiment of the present invention. As illustrated in FIGS. 14 and 15, a fast VT threshold 923 is included within the VT/VF zone 920 in order to discriminate VT from VF events, with the event being identified as a fast VT event when the $O_2$ variation index trend is located between threshold 922 and threshold 923, and as a VF event when the $O_2$ variation index trend is located between threshold 921 and threshold 923.

According to another embodiment of the present invention, a slow VT threshold 925 may also be included in order to discriminate between normal sinus rhythm and slow VT events, with $O_2$ variation index trends that are sustained between threshold 925 and threshold 922 being identified as associated with a slow VT event.

In particular, once the $O_2$ variation index trend is determined to be less than the baseline value 210, Yes in Block 509, and the $O_2$ variation index trend is determined to be within the VT/VF zone 920, Yes in Block 513, as described above, a determination is made as to whether the $O_2$ variation index trend is determined to be sustained within the VT/VF zone 920 for a predetermined time period, Block 515, such as 3-5 samples, for example. If the $O_2$ variation index trend is not sustained VT/VF, No in Block 515, the process returns to Block 502 so that the deviation of the $O_2$ variation index samples from the $O_2$ variation index trend, Blocks 503 and 504 is determined for the next window of $O_2$ variation index samples, described above.

If the $O_2$ variation index trend is sustained VT/VF, Yes in Block 515, the event is identified as a VF event if the $O_2$ variation index trend is located between threshold 921 and threshold 923, and as a VT event if the $O_2$ variation index trend is located between threshold 923 and threshold 922, Block 517. Once the classification of the event is determined in Block 517, delivery of the therapy is adjusted accordingly, Block 519, and the current stored slope values are cleared.

According to an embodiment of the present invention, slow VT threshold 925 may also be included in order to discriminate between normal sinus rhythm and slow VT events. In particular, if the $O_2$ variation index trend is not determined to be within the VT/VF zone, No in Block 513, a determination is made as to whether the $O_2$ variation index trend is located between threshold 925 and threshold 922. If the $O_2$ variation index trend is located between threshold 925 and threshold 922, the event is classified as a slow VT event and the classification may be stored for future reference.

Similar to threshold 921 and threshold 922, both threshold 923 and threshold 925 are programmable. According to an exemplary embodiment of the present invention, threshold 923 corresponds to the $O_2$ variation index trend crossing the baseline value 210 in twelve seconds or less, so that threshold 923 corresponds to a slope of 0.0017 (i.e., 0.02 divided by 12 seconds), and threshold 925 corresponds to the $O_2$ variation index trend crossing the baseline value 210 in 28 or more seconds, so that threshold 925 corresponds to a slope of 0.0007 (i.e., 0.02 divided by 28 seconds).

As described above, when noise is detected, a correction can be made by referring to the corrected $O_2$ variation index trend at a prior instant when the $O_2$ variation index trend was unaffected by noise. Since the determination of noise by measuring deviation of the $O_2$ variation index samples from the $O_2$ variation index trend is done over a window of multiple samples it may be necessary to look back substantially more than a single, immediately prior sample, which may lead to a delay in the determination of the presence of noise from its actual moment of onset. According to an embodiment of the present invention, in order to mitigate any error due to such a delay, the corrected $O_2$ variation index trend consists of multiple values each corresponding to one sample within the sampling window for the determination of the $O_2$ variation index trend, such that when noise is detected in a sampling window, an early value from a previously determined group of values of the corrected $O_2$ variation index trend can be referred to as one belonging to a noise-free period. This particular value of the corrected $O_2$ variation index trend can then be used for computing an offset to correct further $O_2$ variation index trend.

In this embodiment, for each sampling window, a group of corrected $O_2$ variation index trend values are computed and stored in device 14, each value corresponding to one sample of the O$_2$ variation index within the window. The method of computation of the value of the corrected O$_2$ variation index trend depends on the computed deviation during the sampling window, Block 505 of FIG. 9, and, in case of a large deviation indicative of noise, No in Block 505 of FIG. 9, all the corrected O$_2$ variation index trend values for the sampling window are set to the value of the corrected O$_2$ variation index trend corresponding to a predetermined sample of a predetermined prior sampling window such as the first sample, labeled i−1, of the sampling window. In case of a large deviation, No in Block 505 of FIG. 9, the offset is also updated in Block 510 by assigning to it the difference between the value of the O$_2$ variation index trend corresponding to a predetermined sample, such as the sample labeled i+n of the sampling window, and the value of the corrected O$_2$ variation index trend corresponding to a predetermined sample of a predetermined prior sampling window, such as the first sample, labeled i−1, of the sampling window. Such computation may be continued for every sample of the O$_2$ variation index trend where the deviation is large, No in Block 505 of FIG. 9, according to the equation:

$$\text{offset} = tO_{2(m)} - cO_{2(k)}^{-p} \qquad \text{Equation 7}$$

where $tO_{2(m)}$ is the O$_2$ variation index trend value corresponding to the predetermined sample m within the current sampling window and $cO_{2(k)}^{-p}$ is the value of the corrected O$_2$ variation index trend corresponding to the predetermined sample k within a prior sampling window that precedes the current sampling window by a predetermined number of windows indicated by p. The value of the offset so computed is used during the next noise-free sampling window.

In case of a small deviation, Yes in 505 of FIG. 9, indicative of a noise-free sampling window, the corrected O$_2$ variation index trend is computed corresponding to each sample within the interval by taking the difference between the O$_2$ variation index trend corresponding to each sample and the offset computed during the last period of noise.

Since this method depends on the corrected O$_2$ variation index trend from a prior sampling window, it requires initialization of the corrected O$_2$ variation index trend for a certain number of initial sampling windows, the number being same as the predetermined value, p. For each of these windows if the deviation of the O$_2$ variation index samples from its O$_2$ variation index trend is above its threshold for the determination of noise, each value of the corrected O$_2$ variation index trend in that sampling window is set to zero otherwise each value of the corrected O$_2$ variation index trend is set to its corresponding value of the O$_2$ variation index trend.

Determination of the hemodynamic status may be improved by further analyzing the slope of the O$_2$ variation index trend. The slope being referred to here is the slope of the O$_2$ variation index trend line with the time axis which may also be referred to as the rate of change of the O$_2$ variation index trend. Such analysis of the slope will enable determination of the degree of the perfusion loss which may vary between tolerated ventricular tachyarrhythmia, non-tolerated ventricular tachyarrhythmia and ventricular fibrillation. A slope is computed for each sampling window, of 5 second duration consisting of 15 samples for example, and a certain number of the most recent values of it are stored in the device memory. The slope may be defined as the difference between the first and the last O$_2$ variation index trend values, for example $tO_{2(15)} - tO_{2(1)}$ for the sampling window consisting of the 1$^{st}$ through the 15$^{th}$ sample. It may also be defined as the ratio of the difference between the first and the last O$_2$ variation index trend values and the time interval between them. For yet another definition of the slope, the difference and the ratio defined above may be computed over a plurality of subsections within a sampling window and can be further combined to derive a composite slope parameter. A plurality of the slope values so computed are stored in the device memory.

According to an embodiment of the present invention, the range of values of the slope of the corrected O$_2$ variation index trend is divided into predetermined groups corresponding to various cardiac rhythms and a predetermined group of values considered non-physiologic. For example a signed slope value smaller than 0.007 per second, called the physiologic limit, may be considered non-physiologic and any signed slope value larger than −0.00007 per second, called the sinus limit, may be considered to correspond to a hemodynamically stable, benign cardiac rhythm. Any intermediate slope value between these two limits may be considered to correspond to VT or VF. Alternatively, the range of those intermediate slope values may be further subdivided with a hemodynamic stability limit demarcating the boundary separating a hemodynamically stable VT, also called the tolerated VT, from a hemodynamically unstable VT, also called the non-tolerated VT, and VF. The physiologic, sinus and the hemodynamic stability limits also may be patient-specific and determined based on tests such as defibrillation threshold test and other electrophysiologic tests.

The slope of the corrected O$_2$ variation index trend is compared against the predetermined physiologic, sinus and the hemodynamic stability limits to determine the underlying cardiac rhythm and the hemodynamic status of the patient, such as a sinus rhythm, a stable VT, an unstable VT or VF or a non-physiologic signal. If it is determined that the corrected O$_2$ variation index trend does not correspond to VT or VF, No in Block 513 of FIG. 13, any value of the slope stored in the device 14 is removed, and a determination is made as to whether a predetermined episode verification time period has expired, Block 507. If the episode verification time period has not expired, the process returns to Block 502 so that the deviation of O$_2$ variation indexes from the O$_2$ variation index trend, Blocks 503 and 504, is determined for the next window of O$_2$ variation indexes 600.

If on the other hand it is determined that the corrected O$_2$ variation index trend corresponds to VT or VF, Yes in Block 513 of FIG. 13, a determination is also made as to whether it is sustained by collecting additional samples of O$_2$ variation index, Block 502 in FIG. 13, and repeating the subsequent steps for a predetermined number of samples, for example 6, or a predetermined duration, for example 2 seconds, to arrive at the same conclusion, Yes in Block 513. The slope value from each pass through the flow chart during such sustainability determination, 515 in FIG. 13, is stored in the device 14.

The consistency of the corrected O$_2$ variation index trend slope is determined by computing the difference between the maximum and the minimum values of the slopes or the standard deviation or the variance of the values of the slopes. If such values are smaller than a predetermined limit, the rhythm is classified in Block 517 based on the average or the minimum signed value of the slope as either VT and VF or further classified as stable VT or unstable VT and VF and a therapy is determined based on it, Block 519. The stored slope values are removed from the device subsequently, Block 523.

While a particular embodiment of the present invention has been shown and described, modifications may be made. It is therefore intended in the appended claims to cover all such changes and modifications, which fall within the true spirit and scope of the invention.

I claim:

1. A medical device, comprising:
a plurality of sensors sensing cardiac signals;
a physiologic sensor sensing physiologic signals to generate a plurality of variation index samples corresponding to the sensed cardiac signals; and
a microprocessor detecting the presence of a cardiac event in response to the sensed cardiac signals, computing, during the detected presence of the cardiac event, a variation index trend associated with a predetermined number of variation index samples of the plurality of variation index samples, determining the deviation of variation index samples of a current predetermined number of variation index samples from the variation index trend, determining whether the sensed cardiac signals are associated with noise in response to the determined deviation, and confirming the detected presence of the cardiac event in response to the sensed cardiac signals not being associated with noise.

2. The device of claim 1, wherein the physiologic sensor comprises an optical sensor sensing an optical signal to determine tissue oxygenation and the variation index trend corresponds to a measure of change in tissue oxygenation determined in response to the sensed optical signal.

3. The device of claim 1, wherein the microprocessor determines, in response to the sensed cardiac signals not being associated with noise, whether the sensed cardiac signals are associated with an unstable rhythm.

4. The device of claim 3, wherein the microprocessor determines whether the computed variation index trend is less than a predetermined index trend threshold.

5. The device of claim 1, wherein the physiologic sensor comprises an optical sensor generating an optical signal and the variation index trend corresponds to relationships between proportions of red light intensities of the optical signal and infrared light intensities of the optical signal to corresponding baseline intensities.

6. The device of claim 1, wherein the physiologic sensor comprises an optical sensor generating an optical signal and the variation index trend corresponds to $$\frac{i}{i_0} - \frac{i^*}{i_0^*},$$

wherein i is an intensity of red light of the optical signal, i* is an intensity of infrared light of the optical signal, $i_0$ is an intensity of red light baseline, and $i_0^*$ is an intensity of infrared light baseline.

7. A method of determining a cardiac event in a medical device, comprising:
sensing cardiac signals from a plurality of electrodes;
detecting the presence of the cardiac event in response to the sensed cardiac signals;
sensing physiologic signals and acquiring a plurality of variation index samples corresponding to the sensed cardiac signals;
computing, during the detected presence of the cardiac event, a variation index trend associated with a predetermined number of variation index samples of the plurality of variation index samples;
determining deviations of variation index samples of a current predetermined number of variation index samples from the variation index trend;
determining whether the sensed cardiac signals are associated with noise in response to the determined deviations; and
confirming the detected presence of the cardiac event in response to the sensed cardiac signals not being associated with noise.

8. The method of claim 7, wherein the sensed physiologic signal comprises an optical signal and the variation index trend corresponds to a measure of change in tissue oxygenation determined in response to the sensed optical signal.

9. The method of claim 7, further comprising determining, in response to the sensed cardiac signals not being associated with noise, whether the sensed cardiac signals are associated with an unstable rhythm, wherein the determined cardiac event is confirmed in response to the sensed cardiac signals being associated with an unstable rhythm.

10. The method of claim 9, wherein determining whether the sensed cardiac signals are associated with an unstable rhythm comprises determining whether the computed variation index trend is less than a predetermined index trend threshold.

11. The method of claim 7, wherein sensing physiologic signals comprises sensing optical signals and the variation index trend corresponds to relationships between proportions of red light intensities of the optical signals and infrared light intensities of the optical signals to corresponding baseline intensities.

12. The method of claim 7, wherein sensing physiologic signals comprises sensing optical signals and the variation index trend corresponds to $$\frac{i}{i_0} - \frac{i^*}{i_0^*},$$

wherein i is an intensity of red light of the optical signals, i* is an intensity of infrared light of the optical signals, $i_0$ is an intensity of red light baseline, and $i_0^*$ is an intensity of infrared light baseline.

13. The device of claim 1, wherein the microprocessor computes the variation index trend over a moving group of the predetermined number of variation index samples of the plurality of variation index samples, including variation index samples of a previous group of the predetermined number of variation index samples.

14. The method of claim 7, wherein computing the variation index trend comprises computing the variation index trend over a moving group of the predetermined number of variation index samples of the plurality of variation index samples, including variation index samples of a previous group of the predetermined number of variation index samples.

* * * * *